(12) United States Patent
Hochstetler et al.

(10) Patent No.: US 9,506,890 B2
(45) Date of Patent: Nov. 29, 2016

(54) PHYSICAL VAPOR DEPOSITED BIOSENSOR COMPONENTS

(71) Applicant: EASTMAN CHEMICAL COMPANY, Kingsport, TN (US)

(72) Inventors: Spencer Erich Hochstetler, Kingsport, TN (US); Senthil Sambandam, Kingsport, TN (US); Dennis L. Ashford, Gray, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 14/724,563

(22) Filed: May 28, 2015

(65) Prior Publication Data

US 2016/0169827 A1    Jun. 16, 2016

Related U.S. Application Data

(63) Continuation-in-part of application No. 14/572,290, filed on Dec. 16, 2014.

(51) Int. Cl.
| | |
|---|---|
| *G01N 27/327* | (2006.01) |
| *C23C 14/34* | (2006.01) |
| *C23C 14/22* | (2006.01) |
| *C12Q 1/00* | (2006.01) |
| *G01N 27/00* | (2006.01) |
| *G01N 33/543* | (2006.01) |
| *G01N 33/553* | (2006.01) |

(52) U.S. Cl.
CPC .......... *G01N 27/3272* (2013.01); *C12Q 1/006* (2013.01); *C23C 14/22* (2013.01); *C23C 14/34* (2013.01); *G01N 27/00* (2013.01); *G01N 33/5438* (2013.01); *G01N 33/553* (2013.01)

(58) Field of Classification Search
CPC .......................... G01N 27/30; G01N 27/3272
See application file for complete search history.

(56) References Cited

U.S. PATENT DOCUMENTS

| | | | |
|---|---|---|---|
| 5,429,895 A * | 7/1995 | Lian et al. ................... 429/223 |
| 5,484,517 A | 1/1996 | Hopson, Jr. |
| 5,837,354 A | 11/1998 | Ogisu et al. |
| 6,013,170 A | 1/2000 | Meade |
| 6,096,426 A | 8/2000 | Mokerji |
| 6,103,033 A | 8/2000 | Say et al. |
| 6,171,714 B1 | 1/2001 | Bergkessel et al. |

(Continued)

FOREIGN PATENT DOCUMENTS

| | | |
|---|---|---|
| CN | 201697658 U | 1/2011 |
| EP | 0176313 A2 | 4/1986 |

(Continued)

OTHER PUBLICATIONS

Inconel Alloy 600 data sheet, Sep. 2008.*

(Continued)

*Primary Examiner* — Luan Van
*Assistant Examiner* — Steven Rosenwald
(74) *Attorney, Agent, or Firm* — Robert C. Morriss

(57) ABSTRACT

A biosensor component is provided that provides enhanced characteristics for use in biosensors, such as blood glucose sensors. The biosensor component comprises a substrate and a conductive layer coated on the substrate. The conductive layer includes nickel and chromium, such that a combined weight percent of the nickel and chromium in the conductive layer is in the range of 50 to 99 weight percent.

31 Claims, 6 Drawing Sheets

(56) References Cited

U.S. PATENT DOCUMENTS

| | | |
|---|---|---|
| 6,332,900 B1 | 12/2001 | Muffoletto et al. |
| 6,352,781 B1 | 3/2002 | Lohwasser et al. |
| 6,484,045 B1 | 11/2002 | Holker et al. |
| 6,824,974 B2 | 11/2004 | Pisharody et al. |
| 6,855,243 B2 | 2/2005 | Khan |
| 6,859,310 B2 | 2/2005 | Simpson et al. |
| 7,018,523 B2 | 3/2006 | Meade |
| 7,063,776 B2 | 6/2006 | Huang |
| 7,465,597 B2 | 12/2008 | Wegner et al. |
| 7,556,724 B2 | 7/2009 | Huang |
| 7,662,880 B2 | 2/2010 | Xia et al. |
| 7,688,167 B2 | 3/2010 | Paranjpye et al. |
| 7,781,322 B2 | 8/2010 | Ku et al. |
| 8,287,719 B2 | 10/2012 | Bhattacharya |
| 8,372,524 B2 | 2/2013 | Chang et al. |
| 8,420,363 B2 | 4/2013 | Wang et al. |
| 8,424,763 B2 | 4/2013 | Charlton et al. |
| 8,440,563 B2 | 5/2013 | Matsumoto et al. |
| 8,613,822 B2 | 12/2013 | Van Nutt et al. |
| 8,623,153 B2 | 1/2014 | Pruneri et al. |
| 8,795,856 B2 | 8/2014 | Kaiju et al. |
| 8,809,843 B2 | 8/2014 | McKone et al. |
| 2004/0118705 A1* | 6/2004 | Khan ............... G01N 33/558 205/792 |
| 2005/0284758 A1* | 12/2005 | Funke et al. ............. 204/403.02 |
| 2006/0068392 A1 | 3/2006 | Kimura et al. |
| 2008/0083618 A1 | 4/2008 | Neel et al. |
| 2010/0181869 A1 | 7/2010 | Pereira Da Cunha et al. |
| 2010/0213079 A1* | 8/2010 | Willis ............... A61B 5/14532 205/775 |
| 2012/0118735 A1* | 5/2012 | Kim et al. ............... 204/403.02 |
| 2013/0090652 A1 | 4/2013 | Jenson et al. |
| 2013/0118735 A1 | 5/2013 | Jamal et al. |

FOREIGN PATENT DOCUMENTS

| | | |
|---|---|---|
| EP | 1347302 A2 | 9/2003 |
| ES | 2186494 A1 | 1/2003 |
| WO | WO 99/30152 A1 | 6/1999 |
| WO | WO 2010/122270 A1 | 10/2010 |
| WO | WO 2010/123802 A2 | 10/2010 |

OTHER PUBLICATIONS

Inconel Alloy 617 data sheet, Mar. 2005.*
Office Action dated Apr. 17, 2015 received in co-ponding U.S. Appl. No. 14/572,290.
Notification of Transmittal of The International Search Report and The Written Opinion of The International Searching Authority, or the Declaration; International Application No. PCT/US2015/065685 with a filing date of Dec. 15, 2015.

* cited by examiner

PHYSICAL VAPOR DEPOSITED BIOSENSOR COMPONENTS

CROSS-REFERENCE TO RELATED APPLICATIONS

This application is a continuation in part of U.S. nonprovisional application Ser. No. 14/572,290 filed Dec. 16, 2014, the disclosure of which is incorporated herein by reference in its entirety.

BACKGROUND

Field of the Invention

The present invention is generally related to electrodes, for example, physical vapor deposited components for electrodes such as those found in biosensors. More particularly, the present invention is related to electrodes formed with non-noble metal alloys, for example, those found in biosensor components.

Description of the Related Art

Biosensors for use in analyzing biological samples are becoming increasingly prevalent. For example, with the rise in cases of diabetes in the world's population, the need for biosensors for measuring blood glucose has risen dramatically. Such biosensors are generally known as glucometers and operate by having a user place a drop of blood on a test-strip associated with the glucometer. The test-strip is configured to be reactive to the amount of glucose in the drop of blood, such that the glucometer can detect and display a glucose level of the user's blood.

The test-strips for glucometer-type biosensors are generally formed with two or more electrodes (e.g., a working electrode and a counter electrode) formed on a substrate. In addition, an enzyme (e.g., glucose oxidase, glucose dehydrogenase, or the like) and a mediator (e.g., ferricyanide, ruthenium complexes, osmium complexes, quinones, phenothiazines, phenoxazines, or the like) will be formed on the working electrode. In operation, a drop of blood will be applied to a test-strip. Thereafter, an electrochemical reaction proportional to the amount of glucose in the blood will take place on the working electrode. In more detail, glucose first reacts with the enzyme (glucose oxidase, glucose dehydrogenase, or the like) and sometimes an enzyme cofactor (PQQ, FAD, or the like) and is oxidized to gluconic acid. The enzyme, cofactor, or enzyme-cofactor complex is temporarily reduced by two electrons transferred from glucose to the enzyme, cofactor, or enzyme-cofactor complex. Next, the reduced enzyme, cofactor, or enzyme-cofactor complex reacts with the mediator, transferring a single electron to each of two mediator species (molecules or complexes), in the case of a mediator that is reduced in a one-electron process. When the mediator species are reduced, the enzyme, cofactor, or enzyme-cofactor complex is thus returned to its original oxidation state. Then, the reduced mediators diffuse to the electrode surface where a predetermined and sufficiently oxidizing potential is applied to the biosensor so that the reduced mediators are oxidized back to their original oxidation state. The current that is generated by the oxidation of the mediator species by the biosensor is measured and related proportionally to the amount of glucose in the blood.

The quality of the working electrode plays an important role in an accurate measurement of the glucose level of the blood. Specifically, the reproducibility of the electroactive surface area of the electrode, the lot-to-lot repeatability of the electron transfer kinetics of the electrode in a particular glucose measurement arrangement, and long term stability of the electrode material while in storage so that the electrochemical signal that arises from the electrode when the assay is in operation are all factors that lead to improved accuracy of blood glucose test strips. Particularly, it is important that the electrical signals resulting from the electro-activity of the electrode is minimized to prevent bias or noise in the measurement and analysis of biological samples. Typically, this is accomplished by using electrode materials that are intrinsically thermodynamically noble, such as gold, palladium, platinum, iridium, and the like. As such, most current glucometers use electrodes formed from substrates coated with palladium, gold, or other noble metals, generally in the purest form commercially feasible, to function as the working electrode, and for ease of manufacturing, often for the counter electrode or a combined counter and reference electrode. Such noble metals are minimally reactive with interfering substances, and as a result, offer enhanced chemical resistance for consistent and accurate measurements. However, the cost of using such noble metals in electrodes can be prohibitive.

There have been some attempts to use electrodes formed with non-noble metals, so as to reduce manufacturing costs of biosensors. However, such non-noble metal electrodes will generally have an electrochemical response (e.g., dose-responses) that deviates significantly from the electrochemical response of electrodes formed with noble metals. As such, electrodes formed with non-noble metals are generally inadequate for use as direct replacements for noble metals in test-strips for many types of biosensors.

Accordingly, there is a need for an electrode which can be that provides consistent and accurate measurements, while providing a cost effective alternative to the use of noble metals, for example, in biosensors. In particular, there is a need for an electrode formed form a non-noble metal alloy that can be used in a biosensor component to consistently and accurately measure biological samples.

SUMMARY

One or more embodiments of the present disclosure can relate to an electrode which can comprise a substrate and at least one conductive layer coated on the substrate. The conductive layer can comprise nickel and chromium wherein the combined weight percent of the nickel and chromium in the conductive layer can be in the range of 50 to 99 weight percent or 50 to 98 weight percent or 50 to 97 weight percent or 50 to 96 weight percent or 50 to 95 weight percent or 50 to 94 weight percent or 50 to 93 weight percent or 50 to 92 weight percent or 50 to 91 weight percent or 50 to 90 weight percent, based on the total weight of the conductive layer equaling 100 weight percent. While most of this disclosure relates to electrodes used as biosensor components, it is contemplated that the electrodes can be used in other end-use applications as well. As a result, any disclosure herein related to electrodes used in biosensors is intended to incorporate herein applicability to all electrodes that this technology could reasonably be applied to by one of ordinary skill in the art.

One or more embodiments of the present disclosure can relate to a biosensor component which can comprise a substrate and at least one conductive layer coated on the substrate. The conductive layer can comprise nickel and chromium wherein the combined weight percent of the nickel and chromium in the conductive layer can be in the range of 50 to 99 weight percent or 50 to 98 weight percent or 50 to 97 weight percent or 50 to 96 weight percent or 50 to 95 weight percent or 50 to 94 weight percent or 50 to 93 weight percent or 50 to 92 weight percent or 50 to 91 weight percent or 50 to 90 weight percent, based on the total weight of the conductive layer equaling 100 weight percent.

In one embodiment, the present disclosure relates to a biosensor component comprising a substrate and at least one conductive layer coated on the substrate where the conductive layer can comprise nickel in the range of 55 to 60 weight percent and chromium in the range of 15 to 34 weight percent and wherein the total combined weight percent of the nickel and chromium in the conductive layer is in the range of 50 to 99 weight percent or 50 to 98 weight percent or 50 to 97 weight percent or 50 to 96 weight percent or 50 to 95 weight percent or 50 to 94 weight percent or 50 to 93 weight percent or 50 to 92 weight percent or 50 to 91 weight percent or 50 to 90 weight percent, based on the total weight of the conductive layer equaling 100 weight percent.

In one embodiment, the present disclosure relates to a biosensor component comprising a substrate and at least one conductive layer coated on the substrate where the conductive layer can comprise nickel in the range of 55 to 60 weight percent, chromium in the range of 15 to 34 weight percent, and molybdenum in the range of 7 to 17 weight percent and wherein the total combined weight percent of the nickel and chromium in the conductive layer is in the range of 50 to 99 weight percent or 50 to 98 weight percent or 50 to 97 weight percent or 50 to 96 weight percent or 50 to 95 weight percent or 50 to 94 weight percent or 50 to 93 weight percent or 50 to 92 weight percent or 50 to 91 weight percent or 50 to 90 weight, based on the total weight of the conductive layer equaling 100 weight percent.

In one aspect, certain embodiments of the present disclosure relate to a biosensor component comprising a substrate and a conductive layer coated on the substrate wherein the conductive layer can comprise nickel in the range of 56 to 58 weight percent and chromium in the range of 15 to 17 weight percent, wherein the combined weight percent of the nickel and chromium in the conductive layer can be in the range of 50 to 99 weight percent or 50 to 98 weight percent or 50 to 97 weight percent or 50 to 96 weight percent or 50 to 95 weight percent or 50 to 94 weight percent or 50 to 93 weight percent or 50 to 92 weight percent or 50 to 91 weight percent or 50 to 90 weight percent, based on the total weight of the conductive layer equaling 100 weight percent.

In one aspect, certain embodiments of the present disclosure relate to a biosensor component comprising a substrate and a conductive layer coated on the substrate wherein the conductive layer can comprise nickel in the range of 56 to 58 weight percent and chromium in the range of 15 to 17 weight percent, and molybdenum having a weight percent in the range of 15 to 17 weight percent, wherein the combined weight percent of the nickel and chromium in the conductive layer can be in the range of 50 to 99 weight percent or 50 to 98 weight percent or 50 to 97 weight percent or 50 to 96 weight percent or 50 to 95 weight percent or 50 to 94 weight percent or 50 to 93 weight percent or 50 to 92 weight percent or 50 to 91 weight percent or 50 to 90 weight percent, based on the total weight of the conductive layer equaling 100 weight percent.

In one aspect, certain embodiments of the present disclosure relate to a biosensor component comprising a substrate and a conductive layer coated on the substrate wherein the conductive layer can comprise nickel in the range of 54 to 57 weight percent and chromium in the range of 21 to 23 weight percent, wherein the combined weight percent of the nickel and chromium in the conductive layer can be in the range of 50 to 99 weight percent or 50 to 98 weight percent or 50 to 97 weight percent or 50 to 96 weight percent or 50 to 95 weight percent or 50 to 94 weight percent or 50 to 93 weight percent or 50 to 92 weight percent or 50 to 91 weight percent or 50 to 90 weight percent, based on the total weight of the conductive layer equaling 100 weight percent.

In one aspect, certain embodiments of the present disclosure relate to a biosensor component comprising a substrate and a conductive layer coated on the substrate wherein the conductive layer can comprise nickel in the range of 54 to 57 weight percent, chromium in the range of 21 to 23 weight percent, and molybdenum having a weight percent in the range of 12 to 14 weight percent, wherein the combined weight percent of the nickel and chromium in the conductive layer can be in the range of 50 to 99 weight percent or 50 to 98 weight percent or 50 to 97 weight percent or 50 to 96 weight percent or 50 to 95 weight percent or 50 to 94 weight percent or 50 to 93 weight percent or 50 to 92 weight percent or 50 to 91 weight percent or 50 to 90 weight percent, based on the total weight of the conductive layer equaling 100 weight percent.

In one aspect, certain embodiments of the present disclosure relate to a biosensor component comprising a substrate and a conductive layer coated on the substrate wherein the conductive layer can comprise nickel in the range of 58 to 60 weight percent, and chromium in the range of 22 to 24 weight percent, wherein the combined weight percent of the nickel and chromium in the conductive layer can be in the range of 50 to 99 weight percent or 50 to 98 weight percent or 50 to 97 weight percent or 50 to 96 weight percent or 50 to 95 weight percent or 50 to 94 weight percent or 50 to 93 weight percent or 50 to 92 weight percent or 50 to 91 weight percent or 50 to 90 weight percent, based on the total weight of the conductive layer equaling 100 weight percent.

In one aspect, certain embodiments of the present disclosure relate to a biosensor component comprising a substrate and a conductive layer coated on the substrate wherein the conductive layer can comprise nickel in the range of 58 to 60 weight percent, chromium in the range of 22 to 24 weight percent, and molybdenum having a weight percent in the range of 15 to 17 weight percent, wherein the combined weight percent of the nickel and chromium in the conductive layer can be in the range of 50 to 99 weight percent or 50 to 98 weight percent or 50 to 97 weight percent or 50 to 96 weight percent or 50 to 95 weight percent or 50 to 94 weight percent or 50 to 93 weight percent or 50 to 92 weight percent or 50 to 91 weight percent or 50 to 90 weight percent, based on the total weight of the conductive layer equaling 100 weight percent.

In one aspect, certain embodiments of the present disclosure relate to a biosensor component comprising a substrate and a conductive layer coated on the substrate wherein the conductive layer can comprise nickel in the range of 54 to 57 weight percent, chromium in the range of 32 to 34 weight percent, wherein the combined weight percent of the nickel and chromium in the conductive layer can be in the range of 50 to 99 weight percent or 50 to 98 weight percent or 50 to 97 weight percent or 50 to 96 weight percent or 50 to 95 weight percent or 50 to 94 weight percent or 50 to 93 weight percent or 50 to 92 weight percent or 50 to 91 weight percent or 50 to 90 weight percent, based on the total weight of the conductive layer equaling 100 weight percent.

In one aspect, certain embodiments of the present disclosure relate to a biosensor component comprising a substrate and a conductive layer coated on the substrate wherein the conductive layer can comprise nickel in the range of 54 to 57 weight percent, chromium in the range of 32 to 34 weight percent, and molybdenum having a weight percent in the range of 7 to 9 weight percent, wherein the combined weight percent of the nickel and chromium in the conductive layer can be in the range of 50 to 99 weight percent or 50 to 98 weight percent or 50 to 97 weight percent or 50 to 96 weight percent or 50 to 95 weight percent or 50 to 94 weight percent or 50 to 93 weight percent or 50 to 92 weight percent or 50 to 91 weight percent or 50 to 90 weight percent, based on the total weight of the conductive layer equaling 100 weight percent.

In one aspect, certain embodiments of the present disclosure relate to a biosensor component comprising a substrate and a conductive layer coated on the substrate wherein the conductive layer can comprise nickel in the range of 56 to 58 weight percent, chromium in the range of 15 to 17 weight percent, wherein the combined weight percent of the nickel and chromium in the conductive layer can be in the range of 50 to 99 weight percent or 50 to 98 weight percent or 50 to 97 weight percent or 50 to 96 weight percent or 50 to 95 weight percent or 50 to 94 weight percent or 50 to 93 weight percent or 50 to 92 weight percent or 50 to 91 weight percent or 50 to 90 weight percent, based on the total weight of the conductive layer equaling 100 weight percent. The conductive layer can be coated on the substrate, can be comprised of at least one of any polymer described in the art and/or described herein including but not limited to polycarbonate, silicone polymers, acrylics, PET, modified PET such as PETG or PCTG, PCT, modified PCT, polyesters comprising TMCD AND CHDM, PCCD, or PEN, by physical vapor deposition.

In certain embodiments of the disclosure, the conductive layer can have a thickness of between 15 and 200 nm, and the substrate can have a thickness of between 25 and 500 μm. In certain embodiments, the biosensor component can also have visible light transmission of no more than 20% or no more than 15% or no more than 10% or no more than 5 or from 0.01 to 20% or from 0.01 to 15% or from 0.01 10% or from 0.01 to 5%, as measured by ASTM D1003.

In certain embodiments, the conductive layer can have a thickness of between 15 and 200 nm, and the substrate can have a thickness of between 25 and 500 μm wherein the biosensor component has a visible light transmission of no more than 20%.

In certain embodiments, the conductive layer can have a thickness of between 15 and 200 nm, and the substrate can have a thickness of between 25 and 500 μm wherein the biosensor component has a visible light transmission of no more than 15%.

In certain embodiments, the conductive layer can have a thickness of between 15 and 200 nm, and the substrate can have a thickness of between 25 and 500 μm wherein the biosensor component has a visible light transmission of no more than 10%.

In certain embodiments, the conductive layer can have a thickness of between 15 and 200 nm, and the substrate can have a thickness of between 25 and 500 μm wherein the biosensor component has a visible light transmission of no more than 5%.

In one aspect, certain embodiments of the present disclosure relate to a biosensor component comprising a substrate and a conductive layer coated on the substrate wherein the conductive layer can comprise nickel in the range of 56 to 58 weight percent, chromium in the range of 15 to 17 weight percent, and molybdenum having a weight percent in the range of 15 to 17 weight percent, wherein the combined weight percent of the nickel and chromium in the conductive layer can be in the range of 50 to 99 weight percent or 50 to 98 weight percent or 50 to 97 weight percent or 50 to 96 weight percent or 50 to 95 weight percent or 50 to 94 weight percent or 50 to 93 weight percent or 50 to 92 weight percent or 50 to 91 weight percent or 50 to 90 weight percent, based on the total weight of the conductive layer equaling 100 weight percent. The conductive layer is coated on the substrate, which can be comprised of at least one of any polymer described in the art and/or described herein including but not limited to polycarbonate, silicone polymers, acrylics, PET, modified PET such as PETG or PCTG, PCT, PCTA, polyesters comprising TMCD AND CHDM, PCCD, or PEN, by any means known in the art, including but not limited to, physical vapor deposition. The conductive layer has a thickness of between 15 and 200 nm, and the substrate has a thickness of between 25 and 500 μm, such that the biosensor component has a visible light transmission of no more than 20% or no more than 15% or no more than 10% or no more than 5%.

One or more embodiments of the present disclosure can related to an electrode for a biosensor, with the electrode comprising a substrate and a conductive layer coated on the substrate. The conductive layer can comprise nickel and chromium, and the conductive layer can have a dose-response slope, as measured by a Type 1 Chronoamperometry Test, that deviates from a dose-response slope of palladium by no more than 20%.

In one aspect, embodiments of the present disclosure can relate to an electrode for a biosensor, with the electrode comprising a substrate and a conductive layer coated on the substrate. The conductive layer can comprise nickel and chromium, and the conductive layer can have a dose-response slope, as measured by a Type 1 Chronoamperometry Test, that can deviate from a dose-response slope of palladium by no more than 20% or 15% or 10% or 5%. In one embodiment, the conductive layer can comprise nickel having a weight percent in the range of 55 to 60 weight percent and chromium having a weight percent in the range of 15 to 34 weight percent, based on the total weight of the conductive layer equaling 100 weight percent.

In one aspect, embodiments of the present disclosure can relate to an electrode for a biosensor, with the electrode comprising a substrate and a conductive layer coated on the substrate wherein the conductive layer can comprise nickel and chromium, and can have a dose-response slope, as measured by a Type 1 Chronoamperometry Test, that deviates from a dose-response slope of palladium by no more than 20% or 15% or 10% or 5%. The conductive layer can comprise nickel having a weight percent in the range of 55 to 60 weight percent, chromium having a weight percent in the range of 15 to 34 weight percent, and molybdenum having a weight percent in the range of 7 to 17 weight percent, based on the total weight of the conductive layer equaling 100 weight percent.

In one aspect, embodiments of the present disclosure can relate to an electrode for a biosensor, with the electrode comprising a substrate and a conductive layer coated on the substrate wherein the conductive layer can comprise nickel and chromium, and can have a dose-response slope, as measured by a Type 1 Chronoamperometry Test, that can deviate from a dose-response slope of palladium by no more than 20% or 15% or 10% or 5%. In one embodiment, the conductive layer can comprise nickel having a weight percent in the range of 56 to 58 weight percent, and chromium having a weight percent in the range of 15 to 17 weight percent, based on the total weight of the conductive layer equaling 100 weight percent.

In one aspect, embodiments of the present disclosure can relate to an electrode for a biosensor, with the electrode comprising a substrate and a conductive layer coated on the substrate wherein the conductive layer can comprise nickel and chromium, and can have a dose-response slope, as measured by a Type 1 Chronoamperometry Test, that deviates from a dose-response slope of palladium by no more than 20% or 15% or 10% or 5%. In one embodiment, the conductive layer can comprise nickel having a weight percent in the range of 56 to 58 weight percent, chromium having a weight percent in the range of 15 to 17 weight percent, and molybdenum having a weight percent in the range of 15 to 17 weight percent, based on the total weight of the conductive layer equaling 100 weight percent.

In one aspect, embodiments of the present disclosure can relate to an electrode for a biosensor, with the electrode comprising a substrate and a conductive layer coated on the substrate wherein the conductive layer can comprise nickel and chromium, and can have a dose-response slope, as measured by a Type 1 Chronoamperometry Test, that deviates from a dose-response slope of palladium by no more than 20% or 15% or 10% or 5%. The conductive layer can comprise nickel having a weight percent in the range of 54 to 57 weight percent, and chromium having a weight percent in the range of 21 to 23 weight percent, based on the total weight of the conductive layer equaling 100 weight percent.

In one aspect, embodiments of the present disclosure can relate to an electrode for a biosensor, with the electrode comprising a substrate and a conductive layer coated on the substrate wherein the conductive layer can comprise nickel and chromium, and can have a dose-response slope, as measured by a Type 1 Chronoamperometry Test, that deviates from a dose-response slope of palladium by no more than 20% or 15% or 10% or 5%. The conductive layer can comprise nickel having a weight percent in the range of 54 to 57 weight percent, chromium having a weight percent in the range of 21 to 23 weight percent, and molybdenum having a weight percent in the range of 12 to 14 weight percent, based on the total weight of the conductive layer equaling 100 weight percent.

In one aspect, embodiments of the present disclosure can relate to an electrode for a biosensor, with the electrode comprising a substrate and a conductive layer coated on the substrate wherein the conductive layer can comprise nickel and chromium, and can have a dose-response slope, as measured by a Type 1 Chronoamperometry Test, that deviates from a dose-response slope of palladium by no more than 20% or 15% or 10% or 5%. The conductive layer can comprise nickel having a weight percent in the range of 58 to 60 weight percent, and chromium having a weight percent in the range of 22 to 24 weight percent, based on the total weight of the conductive layer equaling 100 weight percent.

In one aspect, embodiments of the present disclosure can relate to an electrode for a biosensor, with the electrode comprising a substrate and a conductive layer coated on the substrate wherein the conductive layer can comprise nickel and chromium, and can have a dose-response slope, as measured by a Type 1 Chronoamperometry Test, that can deviate from a dose-response slope of palladium by no more than 20% or 15% or 10% or 5%. The conductive layer can comprise nickel having a weight percent in the range of 58 to 60 weight percent, chromium having a weight percent in the range of 22 to 24 weight percent, and molybdenum having a weight percent in the range of 15 to 17 weight percent, based on the total weight of the conductive layer equaling 100 weight percent.

In one aspect, embodiments of the present disclosure can relate to an electrode for a biosensor, with the electrode comprising a substrate and a conductive layer coated on the substrate wherein the conductive layer can comprise nickel and chromium, and the conductive layer can have a dose-response slope, as measured by a Type 1 Chronoamperometry Test, that can deviate from a dose-response slope of palladium by no more than 20% or 15% or 10% or 5%. In one embodiment, the conductive layer can comprise nickel having a weight percent in the range of 54 to 57 weight percent, and chromium having a weight percent in the range of 32 to 34 weight percent, based on the total weight of the conductive layer equaling 100 weight percent.

In one aspect, embodiments of the present disclosure can relate to an electrode for a biosensor, with the electrode comprising a substrate and a conductive layer coated on the substrate wherein the conductive layer can comprise nickel and chromium, and can have a dose-response slope, as measured by a Type 1 Chronoamperometry Test, that can deviate from a dose-response slope of palladium by no more than 20% or 15% or 10% or 5%. The conductive layer can comprise nickel having a weight percent in the range of 54 to 57 weight percent, chromium having a weight percent in the range of 32 to 34 weight percent, and molybdenum having a weight percent in the range of 7 to 9 weight percent, based on the total weight of the conductive layer.

One or more embodiments of the present disclosure can relate to an electrode for a biosensor, with the electrode comprising a substrate and a conductive layer coated on the substrate wherein the conductive layer can comprise nickel and chromium, and can have a dose-response slope, as measured by a Type 1 Chronoamperometry Test, that can deviate from a dose-response slope of palladium by no more than 20% or 15% or 10% or 5%. The conductive layer can comprise nickel having a weight percent in the range of 56 to 58 weight percent, chromium having a weight percent in the range of 15 to 17 weight percent, and molybdenum having a weight percent in the range of 15 to 17 weight percent, based on the total weight of the conductive layer. In one embodiment, the conductive layer can be coated on the substrate, which can be comprised of at least one of any polymer described in the art and/or described herein including but not limited to polycarbonate, silicone polymers, acrylics, PET, modified PET such as PETG or PCTG, PCT, PCTA, polyesters comprising TMCD AND CHDM, PCCD, or PEN. by any means known in the art including but not limited to physical vapor deposition. The conductive layer can have a thickness of between 15 and 200 nm, and the substrate can have a thickness of between 25 and 500 µm, such that the biosensor component can have a visible light transmission of no more than 20% or 15% or 10% or 5%.

One or more embodiments of the present disclosure can relate to an electrode for a biosensor, with the electrode comprising a substrate and a conductive layer coated on the substrate wherein the conductive layer can comprise nickel and chromium, and can have a dose-response slope, as measured by a Type 1 Chronoamperometry Test, that can deviate from a dose-response slope of palladium by no more than 20% or 15% or 10% or 5%. The conductive layer can comprise nickel having a weight percent in the range of 56 to 58 weight percent, chromium having a weight percent in the range of 15 to 17 weight percent, and molybdenum having a weight percent in the range of 15 to 17 weight percent, based on the total weight of the conductive layer. The conductive layer can be coated on the substrate, which can be comprised of at least one of any polymer described in the art and/or described herein including but not limited to polycarbonate, silicone polymers, acrylics, PET, modified PET such as PETG or PCTG, PCT, PCTA, polyesters comprising TMCD AND CHDM, PCCD, or PEN, by any means known in the art including but not limited to physical vapor deposition. The conductive layer can have a thickness of between 15 and 200 nm, and the substrate can have a thickness of between 25 and 500 µm, such that the biosensor component can have a visible light transmission of no more than 20% or 15% or 10% or 5%. The electrode can be a working electrode for the biosensor.

One or more embodiments of the present disclosure can relate to an electrode for a blood glucose sensor, with the electrode comprising a substrate and a conductive layer coated on the substrate wherein the conductive layer can comprise nickel and chromium, and have a dose-response slope, as measured by a Type 1 Chronoamperometry Test, that deviates from a dose-response slope of palladium by no more than 10% and wherein the conductive layer can comprise nickel having a weight percent in the range of 56 to 58 weight percent, chromium having a weight percent in the range of 15 to 17 weight percent, and molybdenum having a weight percent in the range of 15 to 17 weight percent, based on the total weight of the conductive layer equaling 100 weight percent. The conductive layer can coated on the substrate, which can be comprised of at least one of any polymer described in the art and/or described herein including but not limited to polycarbonate, silicone polymers, acrylics, PET, modified PET such as PETG or PCTG, PCT, PCTA, polyesters comprising TMCD AND CHDM, PCCD, or PEN, by any means known in the art including but not limited to physical vapor deposition. The conductive layer can have a thickness of between 15 and 200 nm, and the substrate can have a thickness of between 25 and 500 µm, such that the biosensor component can have a visible light transmission of no more than 20% or 15% or 10% or 5%. The electrode can be a working electrode for the biosensor, and the biosensor can be a blood glucose sensor.

The substrate can be comprised of any polymer composition known in the art including but not limited to at least one polymer selected from the groups consisting of: nylon, polyesters, copolyesters, polyethylene, polypropylene, polyamides; polystyrene, polystyrene copolymers, styrene acrylonitrile copolymers, acrylonitrile butadiene styrene copolymers, poly(methylmethacrylate), acrylic copolymers, poly(ether-imides); polyphenylene oxides or poly(phenylene oxide)/polystyrene blends, polystyrene resins; polyphenylene sulfides; polyphenylene sulfide/sulfones; poly(ester-carbonates); polycarbonates; polysulfones; polysulfone ethers; and poly(ether-ketones); or mixtures of any of the other foregoing polymers.

In one embodiment, the substrate can be comprised of at least one polyester comprising residues of at least one glycol selected from the group consisting of ethylene glycol, 1,4-cyclohexanedimethanol, and 2,2,4,4-tetramethyl-1,3-cyclobutanediol.

In one embodiment, the substrate can be comprised of at least one polyester comprising residues of terephthalic acid and/or dimethyl terephthalate and residues of at least one glycol selected from the group consisting of ethylene glycol, 1,4-cyclohexanedimethanol, and 2,2,4,4-tetramethyl-1,3-cyclobutanediol.

In one embodiment, the substrate can be comprised of at least one polyester comprising an acid component which comprises residues of terephthalic acid and isophthalic acid and/or esters thereof such as dimethyl terephthalate, and at glycol component comprising residues of at least one glycol selected from the group consisting of ethylene glycol residues, 1,4-cyclohexanedimethanol residues, and 2,2,4,4-tetramethyl-1,3-cyclobutanediol.

In one embodiment, the substrate can be comprised of at least one polyester comprising terephthalic acid residues, or an ester thereof, or mixtures thereof, and 1,4-cyclohexanedimethanol residues.

In one embodiment, the substrate can be comprised of at least one polyester made from terephthalic acid residues, or an ester thereof, or mixtures thereof, and 1,4-cyclohexanedimethanol residues and/or 2,2,4,4-tetramethyl-1, 3-cyclobutanediol residues.

In one embodiment, the substrate can be comprised of at least one polyester made from terephthalic acid residues, or an ester thereof, or mixtures thereof, 2,2,4,4-tetramethyl-1, 3-cyclobutanediol residues, and 1,4-cyclohexanedimethanol residues.

In one embodiment, the substrate can be comprised of at least one polyester made from terephthalic acid residues, or an ester thereof, or mixtures thereof, 2,2,4,4-tetramethyl-1, 3-cyclobutanediol residues, and ethylene glycol residues.

In one embodiment, the substrate can be comprised of at least one polyester comprising terephthalic acid residues, or an ester thereof, or mixtures thereof, ethylene glycol residues, and 1,4-cyclohexanedimethanol residues.

One or more embodiments of the present disclosure can relate to an electrode for a biosensor, with the electrode comprising a substrate and a conductive layer coated on the substrate wherein the conductive layer can comprise nickel and chromium, and, as measured by a Type 1 Linear Sweep Voltammetry Test, the electrode can be operable to generate a current of less than 0.5 µA at a potential of −60 mV during the sweep, as measured versus a saturated calomel reference electrode, applied to the electrode.

In one aspect, embodiments of the present disclosure can relate to an electrode for a biosensor, with the electrode comprising a substrate and a conductive layer coated on the substrate wherein the conductive layer can comprise nickel and chromium, and, as measured by a Type 1 Linear Sweep Voltammetry Test, the electrode can be operable to generate a current of less than 0.5 µA at a potential of −60 mV during the sweep, as measured versus a saturated calomel reference electrode, applied to the electrode wherein the conductive layer can comprise nickel having a weight percent in the range of 55 to 60 weight percent and chromium having a weight percent in the range of 15 to 34 weight percent, based on the total weight of the conductive layer equaling 100 weight percent.

In one aspect, embodiments of the present disclosure can relate to an electrode for a biosensor, with the electrode comprising a substrate and a conductive layer coated on the substrate wherein the conductive layer can comprise nickel and chromium, and, as measured by a Type 1 Linear Sweep Voltammetry Test, the electrode can be operable to generate a current of less than 0.5 µA at a potential of −60 mV during the sweep, as measured versus a saturated calomel reference electrode, applied to the electrode and wherein the conductive layer can comprise nickel having a weight percent in the range of 55 to 60 weight percent, chromium having a weight percent in the range of 15 to 34 weight percent, and molybdenum having a weight percent in the range of 7 to 17 weight percent, based on the total weight of the conductive layer equaling 100 weight percent.

In one aspect, embodiments of the present disclosure can relate to an electrode for a biosensor, with the electrode comprising a substrate and a conductive layer coated on the substrate wherein the conductive layer can comprise nickel and chromium, and, as measured by a Type 1 Linear Sweep Voltammetry Test, the electrode can be operable to generate a current of less than 0.5 µA at a potential of −60 mV during the sweep, as measured versus a saturated calomel reference electrode, applied to the electrode and wherein the conductive layer can comprise nickel having a weight percent in the range of 56 to 58 weight percent, and chromium having a weight percent in the range of 15 to 17 weight percent, based on the total weight of the conductive layer equaling 100 weight percent.

In one aspect, embodiments of the present disclosure can relate to an electrode for a biosensor, with the electrode comprising a substrate and a conductive layer coated on the substrate wherein the conductive layer can comprise nickel and chromium, and, as measured by a Type 1 Linear Sweep Voltammetry Test, the electrode can be operable to generate a current of less than 0.5 µA at a potential of −60 mV during the sweep, as measured versus a saturated calomel reference electrode, applied to the electrode and wherein the conductive layer can comprise nickel having a weight percent in the range of 56 to 58 weight percent, chromium having a weight percent in the range of 15 to 17 weight percent, and molybdenum having a weight percent in the range of 15 to 17 weight percent, based on the total weight of the conductive layer equaling 100 weight percent.

In one aspect, embodiments of the present disclosure can relate to an electrode for a biosensor, with the electrode comprising a substrate and a conductive layer coated on the substrate wherein the conductive layer can comprise nickel and chromium, and, as measured by a Type 1 Linear Sweep Voltammetry Test, the electrode can be operable to generate a current of less than 0.5 µA at a potential of −60 mV during the sweep, as measured versus a saturated calomel reference electrode, applied to the electrode and wherein the conductive layer can comprise nickel having a weight percent in the range of 54 to 57 weight percent, and chromium having a weight percent in the range of 21 to 23 weight percent, based on the total weight of the conductive layer equaling 100 weight percent.

In one aspect, embodiments of the present disclosure relate to an electrode for a biosensor, with the electrode comprising a substrate and a conductive layer coated on the substrate. The conductive layer can comprise nickel and chromium, and, as measured by a Type 1 Linear Sweep Voltammetry Test, the electrode can be operable to generate a current of less than 0.5 µA at a potential of −60 mV during the sweep, as measured versus a saturated calomel reference electrode, applied to the electrode. The conductive layer can further comprise nickel having a weight percent in the range of 54 to 57 weight percent, chromium having a weight percent in the range of 21 to 23 weight percent, and molybdenum having a weight percent in the range of 12 to 14 weight percent, based on the total weight of the conductive layer equaling 100 weight percent.

In one aspect, embodiments of the present disclosure can relate to an electrode for a biosensor, with the electrode comprising a substrate and a conductive layer coated on the substrate. The conductive layer can comprise nickel and chromium, and, as measured by a Type 1 Linear Sweep Voltammetry Test, the electrode can be operable to generate a current of less than 0.5 µA at a potential of −60 mV during the sweep, as measured versus a saturated calomel reference electrode, applied to the electrode. The conductive layer can further comprise nickel having a weight percent in the range of 58 to 60 weight percent, and chromium having a weight percent in the range of 22 to 24 weight percent, based on the total weight of the conductive layer equaling 100 weight percent.

In one aspect, embodiments of the present disclosure relate to an electrode for a biosensor, with the electrode comprising a substrate and a conductive layer coated on the substrate wherein conductive layer can comprise nickel and chromium, and, as measured by a Type 1 Linear Sweep Voltammetry Test, the electrode can be operable to generate a current of less than 0.5 µA at a potential of −60 mV during the sweep, as measured versus a saturated calomel reference electrode, applied to the electrode. The conductive layer can further comprise nickel having a weight percent in the range of 58 to 60 weight percent, chromium having a weight percent in the range of 22 to 24 weight percent, and molybdenum having a weight percent in the range of 15 to 17 weight percent, based on the total weight of the conductive layer equaling 100 weight percent.

In one aspect, embodiments of the present disclosure relate to an electrode for a biosensor, with the electrode comprising a substrate and a conductive layer coated on the substrate wherein the conductive layer can comprise nickel and chromium, and, as measured by a Type 1 Linear Sweep Voltammetry Test, the electrode can be operable to generate a current of less than 0.5 µA at a potential of −60 mV during the sweep, as measured versus a saturated calomel reference electrode, applied to the electrode. The conductive layer can further comprise nickel having a weight percent in the range of 54 to 57 weight percent, and chromium having a weight percent in the range of 32 to 34 weight percent, based on the total weight of the conductive layer equaling 100 weight percent.

In one aspect, embodiments of the present disclosure relate to an electrode for a biosensor, with the electrode comprising a substrate and a conductive layer coated on the substrate wherein the conductive layer can comprise nickel and chromium, and, as measured by a Type 1 Linear Sweep Voltammetry Test, the electrode can be operable to generate a current of less than 0.5 µA at a potential of −60 mV during the sweep, as measured versus a saturated calomel reference electrode, applied to the electrode. The conductive layer can further comprise nickel having a weight percent in the range of 54 to 57 weight percent, chromium having a weight percent in the range of 32 to 34 weight percent, and molybdenum having a weight percent in the range of 7 to 9 weight percent, based on the total weight of the conductive layer equaling 100 weight percent.

One or more embodiments of the present disclosure can relate to an electrode for a biosensor, with the electrode comprising a substrate and a conductive layer coated on the substrate wherein the conductive layer can comprise nickel and chromium, and, as measured by a Type 1 Linear Sweep Voltammetry Test, the electrode can be operable to generate a current of less than 0.5 µA at a potential of −60 mV during the sweep, as measured versus a saturated calomel reference electrode, applied to the electrode. The conductive layer can further comprise nickel having a weight percent in the range of 56 to 58 weight percent, chromium having a weight percent in the range of 15 to 17 weight percent, and molybdenum having a weight percent in the range of 15 to 17 weight percent, based on the total weight of the conductive layer equaling 100 weight percent. The conductive layer can be coated on a substrate, which can be comprised of any polymer described in the art and/or described herein including but not limited to PET, modified PET such as PETG or PCTG, PCT, polyesters comprising TMCD and CHDM, PCCD, or PEN, by any method known to one of ordinary skill in the art including but not limited to physical vapor deposition. The conductive layer can have a thickness of between 15 and 200 nm, and the substrate can have a thickness of between 25 and 500 µm, such that the biosensor component can have a visible light transmission of no more than 20%.

One or more embodiments of the present disclosure concern an electrode for a biosensor, with the electrode comprising a substrate and a conductive layer coated on the substrate. The conductive layer comprises nickel and chromium, and, as measured by a Type 1 Linear Sweep Voltammetry Test, the electrode is operable to generate a current of less than 0.5 µA at a potential of −60 mV during the sweep, as measured versus a saturated calomel reference electrode, applied to the electrode. The conductive layer can comprise nickel having a weight percent in the range of 56 to 58 weight percent, chromium having a weight percent in the range of 15 to 17 weight percent, and molybdenum having a weight percent in the range of 15 to 17 weight percent, based on the total weight of the conductive layer equaling 100 weight percent. The conductive layer can be coated on the substrate, which can be comprised of any polymer described in the art and/or described herein including but not limited to PET [homopolymer of terephthalic acid (TPA) and ethylene glycol (EG], modified PET such as PETG [PET containing a higher molar percentage of EG than CHDM (1,4-cyclohexanedimethanol)] or PCTG [PET containing a higher molar percentage of EG (ethylene glycol) than CHDM], PCT (polycyclohexylenedimethylene terephthalate), modified PCT, polyesters comprising TMCD (2,2,4,4-tetramethyl-1,3-cyclobutanediol) AND CHDM, PCCD, or PEN, by any means known to one of ordinary skill in the art, including physical vapor deposition. The conductive layer can have a thickness of between 15 and 200 nm, and the substrate can have a thickness of between 25 and 500 µm, such that the biosensor component can have a visible light transmission of no more than 20%. The electrode can be a working electrode for the biosensor.

One or more embodiments of the present disclosure concern an electrode for a biosensor, with the electrode comprising a substrate and a conductive layer coated on the substrate. The conductive layer can comprise nickel and chromium, and, as measured by a Type 1 Linear Sweep Voltammetry Test, the electrode can be operable to generate a current of less than 0.5 µA at a potential of −60 mV during the sweep, as measured versus a saturated calomel reference electrode, applied to the electrode. The conductive layer can further comprise nickel having a weight percent in the range of 56 to 58 weight percent, chromium having a weight percent in the range of 15 to 17 weight percent, and molybdenum having a weight percent in the range of 15 to 17 weight percent, based on the total weight of the conductive layer equaling 100 weight percent. The conductive layer can be coated on the substrate, which can be comprised of any polymer described in the art and/or described herein including but not limited to PET, modified PET such as PETG or PCTG, PCT, modified PCT, polyesters comprising TMCD AND CHDM, PCCD [poly(1,4-cyclohexanedimethanol-1,4-dicarboxylate], or PEN [poly(ethylene-2,6-napthalene dicarboxylate)], by any means known to one of ordinary skill in the art including physical vapor deposition. The conductive layer can have a thickness of between 15 and 200 nm, and the substrate can have a thickness of between 25 and 500 µm, such that the biosensor component can have a visible light transmission of no more than 20%. The electrode can be a working electrode for the biosensor, and the biosensor can be a blood glucose sensor.

Conductive layers in the present disclosure can be constructed of a single layer comprising any of the alloy compositions disclosed in this application. In certain embodiments, the alloy composition contains an alloy which can be a solid solution of the elements (a single phase), a mixture of metallic phases (two or more solutions) or an intermetallic compound with no distinct boundary between the phases.

One or more embodiments of the present disclosure concern a method for forming an electrode for a biosensor. The method comprises (a) providing a substrate; (b) providing a target; and (c) physical vapor depositing at least a portion of said substrate with material from said target to thereby form a conductive layer on said substrate. The conductive material can comprise nickel and chromium, and a combined weight percent of the nickel and chromium in the conductive layer can be in the range of 50 to 99 weight percent. Additionally, the conductive layer can have a sheet resistance of less than 2000 ohms per square.

In one aspect, embodiments of the present disclosure can relate to a method for forming an electrode for a biosensor. The method comprises (a) providing a substrate; (b) providing a target; and (c) physical vapor depositing at least a portion of said substrate with material from said target to thereby form a conductive layer on said substrate. The conductive material can comprise nickel and chromium, and a combined weight percent of the nickel and chromium in the conductive layer can be in the range of 50 to 99 weight percent, based on the total weight of the conductive layer equaling 100 weight percent. The conductive layer can have a sheet resistance of less than 2000 ohms per square. The conductive layer can further comprise nickel having a weight percent in the range of 55 to 60 weight percent and chromium having a weight percent in the range of 15 to 34 weight percent, based on the total weight of the conductive layer equaling 100 weight percent.

In one aspect, embodiments of the present disclosure relate to a method for forming an electrode for a biosensor. The method comprises (a) providing a substrate; (b) providing a target; and (c) physical vapor depositing at least a portion of said substrate with material from said target to thereby form a conductive layer on said substrate. The conductive material can comprise nickel and chromium, and a combined weight percent of the nickel and chromium in the conductive layer can be in the range of 50 to 99 weight percent. The conductive layer can have a sheet resistance of less than 2000 ohms per square. The conductive layer can further comprise nickel having a weight percent in the range of 55 to 60 weight percent, chromium having a weight percent in the range of 15 to 34 weight percent, and molybdenum having a weight percent in the range of 7 to 17 weight percent, based on the total weight of the conductive layer equaling 100 weight percent.

In one aspect, embodiments of the present disclosure relate to a method for forming an electrode for a biosensor. The method comprises (a) providing a substrate; (b) providing a target; and (c) physical vapor depositing at least a portion of said substrate with material from said target to thereby form a conductive layer on said substrate. The conductive material can comprise nickel and chromium, and a combined weight percent of the nickel and chromium in the conductive layer can be in the range of 50 to 99 weight percent, based on the total weight of the conductive layer equaling 100 weight percent. The conductive layer can have a sheet resistance of less than 2000 ohms per square. The conductive layer can further comprise nickel having a weight percent in the range of 56 to 58 weight percent, and chromium having a weight percent in the range of 15 to 17 weight percent, based on the total weight of the conductive layer equaling 100 weight percent.

In one aspect, embodiments of the present disclosure relate to a method for forming an electrode for a biosensor. The method comprises (a) providing a substrate; (b) providing a target; and (c) physical vapor depositing at least a portion of said substrate with material from said target to thereby form a conductive layer on said substrate. The conductive material can comprise nickel and chromium, and a combined weight percent of the nickel and chromium in the conductive layer can be in the range of 50 to 99 weight percent, based on the total weight of the conductive layer equaling 100 weight percent. The conductive layer can have a sheet resistance of less than 2000 ohms per square. The conductive layer can comprise nickel having a weight percent in the range of 56 to 58 weight percent, chromium having a weight percent in the range of 15 to 17 weight percent, and molybdenum having a weight percent in the range of 15 to 17 weight percent, based on the total weight of the conductive layer equaling 100 weight percent.

In one aspect, embodiments of the present disclosure relate to a method for forming an electrode for a biosensor. The method comprises (a) providing a substrate; (b) providing a target; and (c) physical vapor depositing at least a portion of said substrate with material from said target to thereby form a conductive layer on said substrate. The conductive material can comprise nickel and chromium, and a combined weight percent of the nickel and chromium in the conductive layer is in the range of 50 to 99 weight percent, based on the total weight of the conductive layer equaling 100 weight percent. The conductive layer can have a sheet resistance of less than 2000 ohms per square. The conductive layer can further comprise nickel having a weight percent in the range of 54 to 57 weight percent, and chromium having a weight percent in the range of 21 to 23 weight percent, based on the total weight of the conductive layer equaling 100 weight percent.

In one aspect, embodiments of the present disclosure relate to a method for forming an electrode for a biosensor. The method comprises (a) providing a substrate; (b) providing a target; and (c) physical vapor depositing at least a portion of said substrate with material from said target to thereby form a conductive layer on said substrate. The conductive material can comprises nickel and chromium, and a combined weight percent of the nickel and chromium in the conductive layer can be in the range of 50 to 99 weight percent, based on the total weight of the conductive layer equaling 100 weight percent. The conductive layer can have a sheet resistance of less than 2000 ohms per square. The conductive layer can further comprise nickel having a weight percent in the range of 54 to 57 weight percent, chromium having a weight percent in the range of 21 to 23 weight percent, and molybdenum having a weight percent in the range of 12 to 14 weight percent, based on the total weight of the conductive layer equaling 100 weight percent.

In one aspect, embodiments of the present disclosure relate to a method for forming an electrode for a biosensor. The method comprises (a) providing a substrate; (b) providing a target; and (c) physical vapor depositing at least a portion of said substrate with material from said target to thereby form a conductive layer on said substrate. The conductive material can comprise nickel and chromium, and a combined weight percent of the nickel and chromium in the conductive layer is in the range of 50 to 99 weight percent, based on the total weight of the conductive layer equaling 100 weight percent. The conductive layer can have a sheet resistance of less than 2000 ohms per square. The conductive layer can comprise nickel having a weight percent in the range of 58 to 60 weight percent, and chromium having a weight percent in the range of 22 to 24 weight percent, based on the total weight of the conductive layer equaling 100 weight percent.

In one aspect, embodiments of the present disclosure relate to a method for forming an electrode for a biosensor. The method comprises (a) providing a substrate; (b) providing a target; and (c) physical vapor depositing at least a portion of said substrate with material from said target to thereby form a conductive layer on said substrate. The conductive material can comprise nickel and chromium, and a combined weight percent of the nickel and chromium in the conductive layer can be in the range of 50 to 99 weight percent, based on the total weight of the conductive layer equaling 100 weight percent. The conductive layer can have a sheet resistance of less than 2000 ohms per square. The conductive layer can further comprise nickel having a weight percent in the range of 58 to 60 weight percent, chromium having a weight percent in the range of 22 and 24 weight percent, and molybdenum having a weight percent in the range of 15 to 17 weight percent, based on the total weight of the conductive layer equaling 100 weight percent.

In one aspect, embodiments of the present disclosure relate to a method for forming an electrode for a biosensor. The method comprises (a) providing a substrate; (b) providing a target; and (c) physical vapor depositing at least a portion of said substrate with material from said target to thereby form a conductive layer on said substrate. The conductive material can comprise nickel and chromium, and a combined weight percent of the nickel and chromium in the conductive layer can be in the range of 50 to 99 weight percent, based on the total weight of the conductive layer equaling 100 weight percent. The conductive layer can have a sheet resistance of less than 2000 ohms per square. The conductive layer can further comprise nickel having a weight percent in the range of 54 to 57 weight percent, and chromium having a weight percent in the range of 32 to 34 weight percent, based on the total weight of the conductive layer equaling 100 weight percent.

In one aspect, embodiments of the present disclosure relate to a method for forming an electrode for a biosensor. The method comprises (a) providing a substrate; (b) providing a target; and (c) physical vapor depositing at least a portion of said substrate with material from said target to thereby form a conductive layer on said substrate. The conductive material can comprise nickel and chromium, and a combined weight percent of the nickel and chromium in the conductive layer can be in the range of 50 to 99 weight percent, based on the total weight of the conductive layer equaling 100 weight percent. The conductive layer can have a sheet resistance of less than 2000 ohms per square. The conductive layer can comprise nickel having a weight percent in the range of 54 to 57 weight percent, chromium having a weight percent in the range of 32 to 34 weight percent, and molybdenum having a weight percent in the range of 7 to 9 weight percent, based on the total weight of the conductive layer equaling 100 weight percent.

One or more embodiments of the present disclosure concern a method for forming an electrode for a biosensor. The method comprises (a) providing a substrate; (b) providing a target; and (c) physical vapor depositing at least a portion of said substrate with material from said target to thereby form a conductive layer on said substrate. The conductive material can comprise nickel and chromium, and a combined weight percent of the nickel and chromium in the conductive layer can be in the range of 50 to 99 weight percent, based on the total weight of the conductive layer equaling 100 weight percent. The conductive layer can have a sheet resistance, as measured by ASTM F1711-96, of no more than 5000, 2000, 100, 80, 60, 50, 40, 20, 10, or 5 ohms per square. In some embodiments, the conductive layer can have a sheet resistance of between 1 to 5000 ohms per square, 1 to 4000 ohms per square, 1 to 3000 ohms per square, 1 to 2000 ohms per square, 1 to 1000 ohms per square, 1 to 500 ohms per square, 5 to 100 ohms per square, 10 to 80 ohms per square, 20 to 60 ohms per square, or 40 to 50 ohms per square, as measured by ASTM F1711-96. The conductive layer can have a sheet resistance of less than 2000 ohms per square. The conductive layer can further comprise nickel having a weight percent in the range of 56 to 58 weight percent, chromium having a weight percent in the range of 15 to 17 weight percent, and molybdenum having a weight percent in the range of 15 to 17 weight percent, based on the total weight of the conductive layer equaling 100 weight percent. The conductive layer can be coated on the substrate, which can be comprised of any polymer described in the art and/or described herein including but not limited to PET, modified PET such as PETG or PCTG, PCT, modified PCT, polyesters comprising TMCD AND CHDM, PCCD, or PEN, any method known to one of ordinary skill in the art, for example, by physical vapor deposition. The conductive layer can have a thickness of between 15 and 200 nm, and the substrate can have a thickness of between 25 and 500 μm, such that the biosensor component can have a visible light transmission of no more than 20%.

One or more embodiments of the present disclosure concern a method for forming an electrode for a biosensor. The method comprises (a) providing a substrate; (b) providing a target; and (c) physical vapor depositing at least a portion of said substrate with material from said target to thereby form a conductive layer on said substrate. The conductive material can comprise nickel and chromium, and a combined weight percent of the nickel and chromium in the conductive layer can be in the range of 50 to 99 weight percent, based on the total weight of the conductive layer equaling 100 weight percent. The conductive layer can have a sheet resistance of less than 2000 ohms per square. The conductive layer can further comprise nickel having a weight percent in the range of 56 to 58 weight percent, chromium having a weight percent in the range of 15 to 17 weight percent, and molybdenum having a weight percent in the range of 15 to 17 weight percent, based on the total weight of the conductive layer equaling 100 weight percent. The conductive layer is coated on the substrate, which can be comprised of any polymer described in the art and/or described herein including but not limited to PET, modified PET such as PETG or PCTG, PCT, modified PCT, polyesters comprising TMCD AND CHDM, PCCD, or PEN, by any method known to one of ordinary skill in the art, for example, by physical vapor deposition. The conductive layer can have a thickness of between 15 and 200 nm, and the substrate can have a thickness of between 25 and 500 μm, such that the biosensor component can have a visible light transmission of no more than 20%. The electrode can be a working electrode for the biosensor.

One or more embodiments of the present disclosure concern a method for forming an electrode for a biosensor. The method comprises (a) providing a substrate; (b) providing a target; and (c) physical vapor depositing at least a portion of said substrate with material from said target to thereby form a conductive layer on said substrate. The conductive material can comprise nickel and chromium, and a combined weight percent of the nickel and chromium in the conductive layer can be in the range of 50 to 99 weight percent, based on the total weight of the conductive layer equaling 100 weight percent. The conductive layer can have a sheet resistance of less than 2000 ohms per square. The conductive layer can further comprise nickel having a weight percent in the range of 56 to 58 weight percent, chromium having a weight percent in the range of 15 to 17 weight percent, and molybdenum having a weight percent in the range of 15 to 17 weight percent, based on the total weight of the conductive layer equaling 100 weight percent. The conductive layer can be coated on the substrate, which can be comprised of any polymer described in the art and/or described herein including but not limited to PET, modified PET such as PETG or PCTG, PCT, modified PCT, polyesters comprising TMCD AND CHDM, PCCD, or PEN, by any method known to one of ordinary skill in the art, for example, by physical vapor deposition. The conductive layer can have a thickness of between 15 and 200 nm, and the substrate can have a thickness of between 25 and 500 μm, such that the biosensor component can have a visible light transmission of no more than 20%. The electrode can be a working electrode for the biosensor, and the biosensor can be a blood glucose sensor.

BRIEF DESCRIPTION OF THE FIGURES

Embodiments of the present disclosure are described herein with reference to the following figures, wherein.

DETAILED DESCRIPTION

Figure 1:
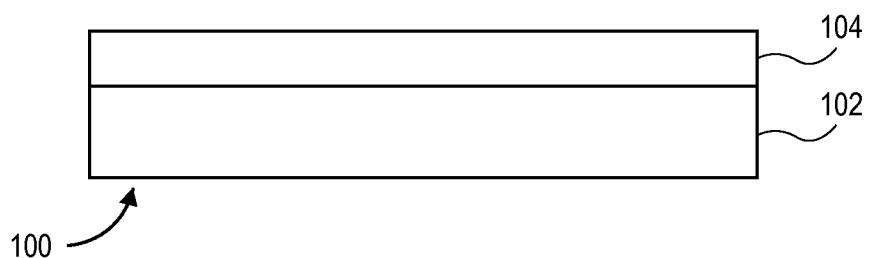
FIG. 1 is a sectional schematic illustration of a thin-film electrode biosensor component of embodiments of the present disclosure.
Figure 2:
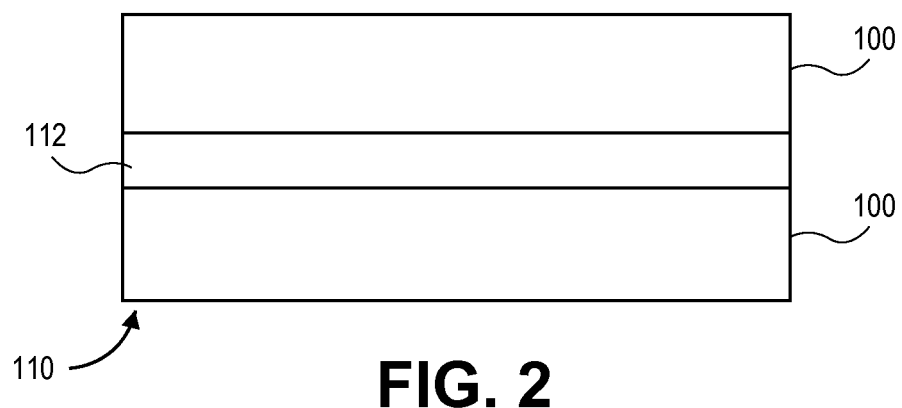
FIG. 2 is a schematic illustration of a test-strip biosensor component of embodiments of the present disclosure.

The present invention is generally directed to a component for an electrode such as those used in a biosensor. As used herein, the term "biosensor" shall denote a device for analyzing biological samples. In some embodiments, as illustrated in FIG. 1, the biosensor component may be a layered thin-film electrode 100 and may broadly comprise a substrate 102 and a conductive layer 104 coated on at least a portion of the substrate 102. In some embodiments, the biosensor may be a medical sensor, such as a glucometer, and the biosensor component may comprise a test-strip for use with the biosensor. As used herein, the term "medical sensor" shall denote a biosensor used for medical monitoring and/or diagnosis. For instance, as illustrated in FIG. 2, some embodiments contemplate that the biosensor component will comprise a test-strip 110 that includes a first electrode 100 separated from a second electrode 100 by a reaction space 112. The first electrode 100 may comprise a working electrode and the second electrode 110 may comprise a reference electrode or a counter electrode or a combined reference and counter electrode. As such, a biological sample, such as a drop of blood, can be placed within the reaction space 112 and in electrical contact with the first and second electrodes 100 for analysis. As used herein, the term "blood glucose sensor" shall denote a medical sensor used to determine a concentration of glucose in blood.

Unlike conventional physical vapor deposited biosensor components, which normally include and/or use noble metals such as palladium and/or gold, the biosensor components described herein can be formed from non-noble metals alloys, such as those including nickel and chromium. Nevertheless, the non-noble metals alloys described herein can exhibit superior consistency and accuracy when measuring biological samples. Thus, by using biosensor components comprised of the non-noble metal alloys described herein, the material and manufacturing costs typically associated with the fabrication and use of biosensor components can be significantly reduced.

Embodiments of the present disclosure provide for the substrate 102 to be formed from any type of material, either flexible or rigid, which is generally non-conductive and chemically inert to the contemplated chemical reactions described herein. In certain embodiments, the substrate 102 of the biosensor component may comprise a flexible, non-conductive film, including polymers, such as a polymeric film, a polyester film, a polycarbonate film, or the like. In certain specific embodiments, the substrate 102 may comprise a polyethylene terephthalate (PET) film. Embodiments of the present disclosure contemplate that the substrate 102 may have a thickness of at least 25 μm, 125 μm, or 250 μm, and/or not more than 800 μm, 500 μm, or 400 μm. In certain embodiments, the substrate 102 may have a thickness of between 25 to 800 μm, 25 to 500 μm, or 25 to 400 μm, between 125 to 800 μm, 125 to 500 μm, or 125 to 400 μm, or between 250 to 800 μm, 250 to 500 μm, or 250 to 400 μm.

The conductive layer 104 coated on the substrate 102 may comprise one or more non-noble metals. Such conductive layer 104 may be coated on the substrate 102 via one or more physical vapor deposition techniques, such as sputter coating (e.g., magnetron sputtering, unbalanced magnetron sputtering, facing targets sputtering, or the like), thermal evaporation, electron beam evaporation, laser ablation, arc vaporization, co-evaporation, ion plating, or the like. The conductive layer 104 may be coated on the substrate 102 to a thickness of at least 1, 10, 15, or 30 nm, and/or not more than 1000, 200, 100, or 50, nm. In certain embodiments, the conductive layer 104 may have a thickness of between 1 to 1000 nm, 1 to 200 nm, 1 to 100 nm, or 1 to 50 nm, between 10 to 1000 nm, 10 to 200 nm, 10 to 100 nm, or 10 to 50 nm, between 15 to 1000 nm, 15 to 200 nm, 15 to 100 nm, or 15 to 50 nm, or between 30 to 1000 nm, 30 to 200 nm, 30 to 100 nm, or 30 to 50 nm.

The conductive layer 104 may be coated on the substrate 102, such that the resulting thin-film electrode 100 will generally be opaque to visible light. For example, the resulting thin-film electrode 100 may have a visible light transmission, as measured by ASTM D1003, of no more than 50%, no more than 40%, no more than 30%, or no more than 20%. In certain embodiments, the resulting thin-film electrode 100 may have a visible light transmission of between 1 to 50%, between 10 to 40%, between 15 to 30%, or about 20%. Additionally, the resulting thin-film electrode 100 may have a sheet resistance, as measured by ASTM F1711-96, of no more than 5000, 2000, 100, 80, 60, 50, 40, 20, 10, or 5 ohms per square. In some embodiments, the resulting thin-film electrode 100 may have a sheet resistance of between 1 to 5000 ohms per square, 2 to 2000 ohms per square, 5 to 100 ohms per square, 10 to 80 ohms per square, 20 to 60 ohms per square, or 40 to 50 ohms per square.

Broadly, the non-noble metals described herein, which form the conductive layer 104, may be comprised of alloys of nickel and chromium. For example, Table 1, below, is illustrative of exemplary non-noble metal alloys that may be used in and/or can comprise the conductive layers 104 of the biosensor components of embodiments of the present disclosure. For example, such non-noble metal alloys may include compositional alloys in the form of Compositions A1-A6, as such compositions are defined in Table 1. Table, 1 below, also lists Compositions B1-B5, C1-C9, D1-D3, and E1-E2 and provides ranges for the amounts of selected components in those compositions. In contrast to Compositions A1-A6, which each define a single unique composition, each of Compositions B1-B5, C1-C9, D1-D3, and E1-E2 can encompass multiple different compositions falling within the numerical ranges for the recited components.

TABLE 1

| | Elemental Composition by Weight Percent | | | | | | | |
|---|---|---|---|---|---|---|---|---|
| Composition | Ni | Cr | Ni + Cr | Mo | Fe | Co | Mn | W |
| A1 | 65 | 1.5 | 66.5 | 28.5 | 1.5 | 0-3 | 0-3 | 0-3 |
| A2 | 65 | 8 | 73 | 25 | 0-2 | 0-2.5 | 0-0.8 | 0 |
| A3 | 57 | 16 | 73 | 16 | 5 | 0-2.5 | 0-1 | 4 |
| A4 | 56 | 22 | 78 | 13 | 3 | 0-2.5 | 0-0.5 | 3 |
| A5 | 59 | 23 | 82 | 16 | 0-3 | 0-2 | 0-0.5 | 0 |
| A6 | 55.5 | 33 | 88.5 | 8 | 0-2 | 0 | 0-0.5 | 0 |
| B1 | 30-95 | 0.5-60 | 50-90 | * | * | * | * | * |
| B2 | 30-95 | 0.5-60 | * | 1-50 | * | * | * | * |
| B3 | 30-95 | 0.5-60 | 50-90 | 1-50 | * | * | * | * |
| B4 | 30-95 | 0.5-60 | 50-90 | 1-50 | 0.25-20 | * | 0.1-5 | * |
| B5 | 30-95 | 0.5-60 | 50-90 | 1-50 | 0.25-20 | 0-10 | 0.1-5 | 0-10 |
| C1 | 30-95 | 10-50 | * | 1-50 | * | * | * | * |
| C2 | 30-64 | 0.5-60 | * | * | * | * | * | * |
| C3 | 30-62 | 0.5-60 | * | * | * | * | * | * |
| C4 | 30-64 | 0.5-60 | 50-90 | 1-50 | 0.25-20 | * | 0.1-5 | * |
| C5 | 30-62 | 0.5-60 | 50-90 | 1-50 | 0.25-20 | 0-10 | 0.1-5 | 0-10 |

TABLE 1-continued

| | | | | | | | | |
|---|---|---|---|---|---|---|---|---|
| C6 | 30-95 | 0.5-60 | * | 1-24 | * | * | * | * |
| C7 | 30-95 | 0.5-60 | * | 2-20 | * | * | * | * |
| C8 | 30-95 | 0.5-60 | * | 1-24 | 0.25-20 | * | 0.1-5 | * |
| C9 | 30-95 | 0.5-60 | 50-90 | 2-20 | 0.25-20 | 0-10 | 0.1-5 | 0-10 |
| D1 | 30-95 | 10-30 | * | 5-30 | * | * | * | * |
| D2 | 50-70 | 10-50 | 50-90 | 5-30 | 0.25-20 | 0.5-10 | * | * |
| D3 | 50-70 | 10-50 | 50-90 | 5-30 | 0.25-20 | 0.5-10 | 0.1-5 | 0-10 |
| E1 | 30-95 | 10-30 | 50-80 | 15-30 | * | * | * | * |
| E2 | 50-70 | 5-30 | 50-90 | 15-30 | 0.25-20 | 0.5-10 | 0.1-5 | 0.5-10 |

| | Elemental Composition by Weight Percent | | | | | | |
|---|---|---|---|---|---|---|---|
| Composition | Si | C | Al | Cu | Ti | B | V |
| A1 | 0-0.1 | 0-0.01 | 0.5 | 0 | 0.2 | 0 | 0 |
| A2 | 0-0.8 | 0-0.03 | 0-0.5 | 0-0.5 | 0 | 0-.006 | 0 |
| A3 | 0-0.08 | 0-0.01 | 0 | 0 | 0 | 0 | 0-0.35 |
| A4 | 0-0.08 | 0-0.01 | 0 | 0 | 0 | 0 | 0-0.35 |
| A5 | 0-0.08 | 0-0.01 | 0 | 1.6 | 0 | 0 | 0 |
| A6 | 0-0.6 | 0-0.05 | 0-0.4 | 0 | 0 | 0 | 0 |
| B1 | * | * | * | * | * | * | * |
| B2 | * | * | * | * | * | * | * |
| B3 | * | * | * | * | * | * | * |
| B4 | * | * | * | * | * | * | * |
| B5 | 0.01-5 | 0.001-2 | 0-2 | 0-2 | * | * | * |
| C1 | * | * | * | * | * | * | * |
| C2 | * | * | * | * | * | * | * |
| C3 | * | * | * | * | * | * | * |
| C4 | * | * | * | * | * | * | * |
| C5 | 0.01-5 | 0.001-2 | 0-2 | 0-2 | * | * | * |
| C6 | * | * | * | * | * | * | * |
| C7 | * | * | * | * | * | * | * |
| C8 | * | * | * | * | * | * | * |
| C9 | 0.01-5 | 0.001-2 | 0-2 | 0-2 | * | * | * |
| D1 | * | * | * | * | * | * | * |
| D2 | * | * | * | * | * | * | * |
| D3 | 0.01-5 | 0.001-2 | 0-2 | 0-2 | * | * | * |
| E1 | * | * | * | * | * | * | * |
| E2 | 0.01-5 | 0.001-2 | 0-2 | 0-2 | * | * | * |

* Optionally component or amount not specified

In addition to the amounts described above in Table 1, in certain embodiments, the amount of nickel and chromium included in the non-noble metal alloys that comprise the conductive layer of the electrode (for example, conductive layer 104 of the biosensor component) can vary depending on the specific requirements of the electrode, for example, the biosensor component. In various embodiments, the non-noble metal alloys can comprise at least about 30, 40, 50, or 55 and/or up to about 95, 85, 75, 65, or 60 weight percent of nickel. In certain embodiments, the non-noble metal alloys can comprise in the range of about 30 to 99, 30 to 95, 50 to 99, 50 to 98, 50 to 97, 50 to 96, 50 to 95, 50 to 75, or 55 to 60 weight percent of nickel. Additionally, in various embodiments, the non-noble metal alloys can comprise at least about 0.5, 1, 2, 5, 10, or 15 and/or up to about 60, 50, 40, 35, 30, and 25 weight percent of chromium. More particularly, the non-noble metal alloys can comprise in the range of about 0.5 to 60, 5 to 35, or 15 to 25 weight percent of chromium.

In certain embodiments, the amount of nickel and chromium included in the non-noble metal alloys that comprise the conductive layer of electrode, for example, the biosensor component, can vary depending on the specific requirements of the biosensor component as follows: 10 to 99 weight % chromium and 1 to 90 weight % nickel; or 10 to 95 weight % chromium and 5 to 90 weight % nickel; or 10 to 90 weight % chromium and 10 to 90 weight % nickel; or 10 to 85 weight % chromium and 15 to 90 weight % nickel; or 10 to 80 weight % chromium and 20 to 90 weight % nickel, or 10 to 75 weight % chromium and 25 to 90 weight % nickel; or 10 to 70 weight % chromium and 30 to 90 weight % nickel; or 10 to 65 weight % chromium and 35 to 90 weight % nickel; or 10 to 60 weight % chromium and 40 to 90 weight % nickel; or 10 to 55 weight % chromium and 45 to 90 weight % nickel; or 10 to 50 weight chromium and 50 to 90 weight % nickel; or 10 to 45 weight % chromium and 55 to 90 weight % nickel; or 10 to 40 weight % chromium and 60 to 90 weight % nickel; or 10 to 35 weight % chromium and 65 to 90 weight % nickel; or 10 to 30 weight % chromium and 70 to 90 weight % nickel; or 10 to 25 weight chromium and 75 to 90 weight % nickel; or 10 to 20 weight % chromium and 80 to 90 weight % nickel; or 10 to 15 weight % chromium and 85 to 90 weight % nickel; or 15 to 99 weight % chromium and 1 to 85 weight % nickel; or 15 to 95 weight % chromium and 5 to 85 weight % nickel; or 15 to 90 weight % chromium and 10 to 85 weight % nickel; or 15 to 85 weight % chromium and 15 to 85 weight % nickel; or 15 to 80 weight % chromium and 20 to 85 weight % nickel; or 15 to 75 weight % chromium and 25 to 85 weight % nickel; or 15 to 70 weight % chromium and 30 to 85 weight % nickel; or 15 to 65 weight % chromium and 35 to 85 weight % nickel; or 15 to 60 weight % chromium and 40 to 85 weight % nickel; or 15 to 55 weight % chromium and 45 to 85 weight % nickel; or 15 to 50 weight % chromium and 50 to 85 weight % nickel; or 15 to 45 weight % chromium and 55 to 85 weight % nickel; or 15 to 40 weight % chromium and 60 to 85 weight % nickel; or 15 to 35 weight % chromium and 65 to 85 weight % nickel; or 15 to 30 weight % chromium and 70 to 85 weight % nickel; or 15 to 25 weight % chromium and 75 to 85 weight % nickel; or 20 to 99 weight % chromium and 1 to 80 weight % nickel; or 20 to 95 weight % chromium and 5 to 80 weight % nickel; or 20 to 90 weight % chromium and 10 to 80 weight % nickel; or 20 to 85 weight % chromium and 15 to 80 weight % nickel; or 20 to 80 weight % chromium and 20 to 80 weight % nickel, or 20 to 75 weight % chromium and 25 to 80 weight % nickel; or 20 to 70 weight % chromium and 30 to 80 weight % nickel; or 20 to 65 weight % chromium and 35 to 80 weight % nickel; or 20 to 60 weight % chromium and 40 to 80 weight % nickel; or 20 to 55 weight % chromium and 45 to 80 weight % nickel; or 20 to 50 weight % chromium and 50 to 80 weight % nickel; or 20 to 45 weight % chromium and 55 to 80 weight % nickel; or 20 to 40 weight % chromium and 60 to 80 weight % nickel; or 20 to 35 weight % chromium and 65 to 80 weight % nickel; or 20 to 30 weight % chromium and 70 to 80 weight % nickel; or 25 to 99 weight % chromium and 1 to 75 weight % nickel; or 25 to 90 weight % chromium and 10 to 75 weight % nickel; or 25 to 85 weight % chromium and 15 to 75 weight % nickel; or 25 to 80 weight % chromium and 20 to 75 weight % nickel; or 25 to 75 weight % chromium and 25 to 75 weight % nickel; or 25 to 70 weight % chromium and 30 to 75 weight % nickel; or 25 to 65 weight % chromium and 35 to 75 weight % nickel; or 25 to 60 weight % chromium and 40 to 75 weight % nickel; or 25 to 55 weight % chromium and 45 to 75 weight % nickel; or 25 to 50 weight % chromium and 50 to 75 weight % nickel; or 25 to 45 weight % chromium and 55 to 75 weight % nickel; or 25 to 40 weight % chromium and 60 to 75 weight % nickel; or 25 to 35 weight % chromium and 65 to 75 weight % nickel; or 30 to 99 weight % chromium and 1 to 70 weight % nickel; or 30 to 95 weight % chromium and 5 to 70 weight % nickel; or 30 to 90 weight % chromium and 10 to 70 weight % nickel; or 30 to 85 weight % chromium and 15 to 70 weight % nickel; or 30 to 80 weight % chromium and 20 to 70 weight % nickel or 30 to 75 weight % chromium and 25 to 70 weight % nickel; or 30 to 70 weight % chromium and 30 to 70 weight % nickel; or 30 to 65 weight % chromium and 35 to 70 weight % nickel; or 30 to 60 weight % chromium and 40 to 70 weight % nickel; or 30 to 65 weight % chromium and 35 to 70 weight % nickel; or 30 to 50 weight % chromium and 50 to 70 weight % nickel; or 30 to 45 weight % chromium and 55 to 70 weight % nickel; or 30 to 40 weight % chromium and 60 to 70 weight % nickel; or 35 to 99 weight % chromium and 1 to 65 weight % nickel; or 35 to 95 weight % chromium and 5 to 65 weight % nickel; or 35 to 90 weight % chromium and 10 to 65 weight % nickel; or 35 to 85 weight % chromium and 15 to 65 weight % nickel; or 35 to 80 weight % chromium and 20 to 65 weight % nickel, or 35 to 75 weight % chromium and 25 to 65 weight % nickel; or 35 to 70 weight % chromium and 30 to 65 weight % nickel; or 35 to 65 weight % chromium and 35 to 65 weight % nickel; or 35 to 60 weight % chromium and 40 to 65 weight % nickel; or 35 to 55 weight % chromium and 45 to 65 weight % nickel; or 35 to 50 weight % chromium and 50 to 65 weight % nickel; or 35 to 45 weight % chromium and 55 to 65 weight % nickel; or 40 to 99 weight % chromium and 1 to 60 weight % nickel; or 40 to 95 weight % chromium and 5 to 60 weight % nickel; or 40 to 90 weight % chromium and 10 to 60 weight % nickel; or 40 to 85 weight % chromium and 15 to 60 weight % nickel; or 40 to 80 weight % chromium and 20 to 60 weight % nickel, or 40 to 75 weight % chromium and 25 to 60 weight % nickel; or 40 to 70 weight % chromium and 30 to 60 weight % nickel; or 40 to 65 weight % chromium and 35 to 60 weight % nickel; or 40 to 60 weight % chromium and 40 to 60 weight % nickel; or 40 to 55 weight % chromium and 45 to 60 weight % nickel; or 40 to 50 weight % chromium and 50 to 60 weight % nickel; or 45 to 99 weight % chromium and 1 to 55 weight % nickel; or 45 to 95 weight % chromium and 5 to 55 weight % nickel; or 45 to 90 weight % chromium and 10 to 55 weight % nickel; or 45 to 85 weight % chromium and 15 to 55 weight % nickel; or 45 to 80 weight % chromium and 20 to 55 weight % nickel, or 45 to 75 weight % chromium and 25 to 55 weight % nickel; or 45 to 70 weight % chromium and 30 to 55 weight % nickel; or 45 to 65 weight % chromium and 35 to 55 weight % nickel; or 45 to 60 weight % chromium and 40 to 55 weight % nickel; or 45 to 55 weight % chromium and 45 to 55 weight % nickel; or 50 to 99 weight % chromium; or 40 to 45 weight % chromium and 55 to 60 weight % nickel; and 1 to 50 weight % nickel; or 50 to 98 weight % chromium and 2 to 50 weight % nickel; or 50 to 97 weight % chromium and 3 to 50 weight % nickel; or 50 to 96 weight % chromium and 4 to 50 weight % nickel; or 50 to 95 weight % chromium and 5 to 50 weight % nickel; or 50 to 94 weight % chromium and 6 to 50 weight % nickel; or 50 to 93 weight % chromium and 7 to 50 weight % nickel; or 50 to 92 weight % chromium and 8 to 50 weight % nickel; or 50 to 91 weight % chromium and 9 to 50 weight % nickel; or 50 to 90 weight % chromium and 10 to 50 weight % nickel; or 50 to 85 weight % chromium and 15 to 50 weight % nickel; or 50 to 80 weight % chromium and 20 to 50 weight % nickel, or 50 to 75 weight % chromium and 25 to 50 weight % nickel; or 50 to 70 weight % chromium and 30 to 50 weight % nickel; or 50 to 65 weight % chromium and 35 to 50 weight % nickel; or 50 to 60 weight % chromium and 40 to 50 weight % nickel; or 55 to 99 weight % chromium and 1 to 45 weight % nickel; or 55 to 95 weight % chromium and 5 to 45 weight % nickel; or 55 to 90 weight % chromium and 10 to 45 weight % nickel; or 55 to 85 weight % chromium and 15 to 45 weight % nickel; or 55 to 80 weight % chromium and 20 to 45 weight % nickel, or 55 to 75 weight % chromium and 25 to 45 weight % nickel; or 55 to 70 weight % chromium and 30 to 45 weight % nickel; or 55 to 65 weight % chromium and 35 to 45 weight % nickel; or 60 to 99 weight % chromium and 1 to 40 weight % nickel; or 60 to 95 weight % chromium and 5 to 40 weight % nickel; or 60 to 90 weight % chromium and 10 to 40 weight % nickel; or 60 to 85 weight % chromium and 15 to 40 weight % nickel; or 60 to 80 weight % chromium and 20 to 40 weight % nickel, or 60 to 75 weight % chromium and 25 to 40 weight % nickel; or 60 to 70 weight % chromium and 30 to 40 weight % nickel; or 65 to 99 weight % chromium and 1 to 35 weight % nickel; or 65 to 95 weight % chromium and 5 to 35 weight % nickel; or 65 to 90 weight % chromium and 10 to 35 weight % nickel; or 65 to 85 weight % chromium and 15 to 35 weight % nickel; or 65 to 80 weight % chromium and 20 to 35 weight % nickel; or 65 to 75 weight % chromium and 25 to 35 weight % nickel; or 70 to 99 weight % chromium and 1 to 30 weight % nickel; or 70 to 95 weight % chromium and 5 to 30 weight % nickel; or 70 to 90 weight % chromium and 10 to 30 weight % nickel; or 70 to 85 weight % chromium and 15 to 30 weight % nickel; or 70 to 80 weight % chromium and 20 to 30 weight % nickel; or 75 to 99 weight % chromium and 1 to 25 weight % nickel; or 75 to 95 weight % chromium and 5 to 25 weight % nickel; or 75 to 90 weight % chromium and 10 to 25 weight % nickel; or 75 to 85 weight % chromium and 15 to 25 weight % nickel; or 80 to 99 weight % chromium and 1 to 20 weight % nickel; or 80 to 95 weight % chromium and 5 to 20 weight % nickel; or 80 to 90 weight % chromium and 10 to 20 weight % nickel; or 80 to 85 weight % chromium and 10 to 15 weight % nickel; or 85 to 99 weight % chromium and 1 to 15 weight % nickel; or 85 to 95 weight % chromium and 5 to 15 weight % nickel; or 85 to 90 weight % chromium and 10 to 15 weight % nickel; or 90 to 99 weight % chromium and 1 to 10 weight % nickel; or 90 to 98 weight % chromium and 2 to 10 weight % nickel; or 90 to 97 weight % chromium and 3 to 10 weight % nickel; or 90 to 96 weight % chromium and 4 to 10 weight % nickel; or 90 to 95 weight % chromium and 5 to 10 weight % nickel; or 90 to 94 weight % chromium and 6 to 10 weight % nickel; or 90 to 93 weight % chromium and 7 to 10 weight % nickel; or 90 to 92 weight % chromium and 8 to 10 weight % nickel; or 90 to 91 weight % chromium and 9 to 10 weight % nickel; or 15 to 34 weight % chromium and 55 to 60 weight % nickel; or 15 to 17 weight % chromium and 56 to 58 weight nickel; or 21 to 23 weight % chromium and 54 to 57 weight % nickel; or 22 to 24 weight % chromium and 58 to 60 weight % nickel; or 32 to 34 weight chromium and 54 to 57 weight % nickel; all of these weight percentages being based on the total weight percentages of the conductive layer equaling 100 weight percent.

Non-noble metal alloys other than nickel and chromium that can be present in the invention can include Group I as follows: molybdenum, cobalt, iron, tungsten, manganese, copper, aluminum, titanium, boron, and vanadium. Non-noble metals alloys other than nickel and chromium that can be present are in Group II and include carbon and silicon. Weight percentages of all metal alloys useful in this invention are based on the total weight percentages of materials in the conductive layer equaling 100 weight percent.

Group I non-noble metal alloys that can be used in the invention may be present in an amount up to 89 weight %, based on the total weight percentages of the conductive layer equaling 100 weight percent.

In certain embodiment, other non-noble metals of Group I can be present in the invention in the amount of from 0.01 to 89 weight %; 0.01 to 85 weight %; or 0.01 to 80 weight; or 0.01 to 75 weight %; or 0.01 to 70 weight %; or 0.01 to 65 weight %; or 0.01 to 60 weight %; or 0.01 to 55 weight %; or 0.01 to 50 weight %; or 0.01 to 45 weight %; or 0.01 to 40 weight %; or 0.01 to 35 weight %; or 0.01 to 30 weight %; or 0.01 to 25 weight %; or 0.01 to 20 weight %; or 0.01 to 15 weight %; or 0.01 to 10 weight %; or 0.01 to 5 weight %; 1 to 89 weight %; 1 to 85 weight %; or 1 to 80 weight; or 1 to 75 weight %; or 1 to 70 weight %; or 1 to 65 weight %; or 1 to 60 weight %; or 1 to 55 weight %; or 1 to 50 weight %; or 1 to 45 weight %; or 1 to 40 weight %; or 1 to 35 weight %; or 1 to 30 weight %; or 1 to 25 weight %; or 1 to 20 weight %; or 1 to 15 weight %; or 1 to 10 weight %; 1 to 9 weight %; or 1 to 8 weight percent; or 1 to 7 weight percent; or 1 to 6 weight %; or 1 to 5 weight %; 5 to 89 weight %; 5 to 85 weight %; or 5 to 80 weight; or 5 to 75 weight %; or 5 to 70 weight %; or 5 to 65 weight %; or 5 to 60 weight %; or 5 to 55 weight %; or 5 to 50 weight %; or 5 to 45 weight %; or 5 to 40 weight %; or 5 to 35 weight %; or 5 to 30 weight %; or 5 to 25 weight %; or 5 to 20 weight %; or 5 to 15 weight %; or 5 to 10 weight %; or 5 to 9 weight %; or 5 to 8 weight percent; or 5 to 7 weight percent; 6 to 89 weight %; 6 to 85 weight %; or 6 to 80 weight; or 6 to 75 weight %; or 6 to 70 weight %; or 6 to 65 weight %; or 6 to 60 weight %; or 6 to 55 weight %; or 6 to 50 weight %; or 6 to 45 weight %; or 6 to 40 weight %; or 6 to 35 weight %; or 6 to 30 weight %; or 6 to 25 weight %; or 6 to 20 weight %; or 6 to 15 weight %; or 6 to 10 weight %; or 6 to 9 weight %; or 6 to 8 weight percent; or 10 to 89 weight %; or 10 to 85 weight %; or 10 to 80 weight; or 10 to 75 weight %; or 10 to 70 weight %; or 10 to 65 weight %; or 10 to 60 weight %; or 10 to 55 weight %; or 10 to 50 weight %; or 10 to 45 weight %; or 10 to 40 weight %; or 10 to 35 weight %; or 10 to 30 weight %; or 10 to 25 weight %; or 10 to 20 weight %; or 10 to 15 weight %; or 15 to 89 weight %; or 15 to 85 weight %; or 15 to 80 weight %; or 15 to 75 weight %; or 15 to 70 weight %; or 15 to 65 weight %; or 15 to 60 weight %; or 15 to 55 weight %; or 15 to 50 weight %; or 15 to 45 weight %; or 15 to 40 weight %; or 15 to 35 weight %; or 15 to 30 weight %; or 15 to 25 weight %; or 20 to 89 weight %; or 20 to 85 weight %; or 20 to 80 weight; or 20 to 75 weight %; or 20 to 70 weight %; or 20 to 65 weight %; or 20 to 60 weight %; or 20 to 55 weight %; or 20 to 50 weight %; or 20 to 45 weight %; or 20 to 40 weight %; or 20 to 35 weight %; or 20 to 30 weight %; or 25 to 89 weight %; or 25 to 85 weight %; or 25 to 80 weight %; or 25 to 75 weight %; or 25 to 70 weight %; or 25 to 65 weight %; or 25 to 60 weight %; or 25 to 55 weight %; or 25 to 50 weight %; or 25 to 45 weight %; or 25 to 40 weight %; or 25 to 35 weight %; or 30 to 89 weight %; or; or 30 to 85 weight %; or 30 to 80 weight % or 30 to 75 weight %; or 30 to 70 weight %; or 30 to 65 weight %; or 30 to 60 weight %; or 30 to 65 weight %; or 30 to 50 weight %; or 30 to 45 weight %; or 30 to 40 weight %; or 35 to 89 weight %; or 35 to 85 weight %; or 35 to 80 weight %, or 35 to 75; or 35 to 70 weight %; or 35 to 65 weight %; or 35 to 60 weight %; or 35 to 55 weight %; or 35 to 50 weight %; or 35 to 45 weight %; or 40 to 89 weight %; or 40 to 85 weight %; or 40 to 80 weight %, or 40 to 75 weight %; or 40 to 70 weight %; or 40 to 65 weight %; or 40 to 60 weight %; or 40 to 55 weight %; or 40 to 50 weight %; or 45 to 89 weight %; or 45 to 85 weight %; or 45 to 80 weight %, or 45 to 75 weight %; or 45 to 70 weight %; or 45 to 65; or 45 to 60 weight %; or 45 to 55 weight %; or 50 to 89 weight; or 50 to 85 weight %; or 50 to 80 weight %, or 50 to 75 weight %; or 50 to 70 weight %; or 50 to 65 weight %; or 50 to 60 weight %; or 55 to 89 weight %; or 55 to 85 weight and 25 to 45 weight % nickel; or 55 to 70 weight %; or 55 to 65 weight %; or 60 to 89 weight %; or 60 to 85 weight %; or 60 to 80 weight %, or 60 to 75 weight %; or 60 to 70 weight %; or 65 to 89 weight %; or 65 to 85 weight %; or 65 to 80 weight %; or 65 to 75 weight %; or 70 to 89 weight %; or 70 to 85 weight %; or 70 to 80 weight %; or 75 to 89 weight %; or 75 to 85 weight %; or 80 to 89 weight %; all of these weight percentages being based on the total weight percentages of the conductive layer equaling 100 weight percent.

In various embodiments, the non-noble metal alloys of Group can comprise molybdenum. The presence of molybdenum in the non-noble metal alloys can comprise, for example, at least about 2, 4, 6, 8, 10, or 12 and/or up to about 50, 40, 30, 25, or 20 weight percent of molybdenum. More particularly, the non-noble metal alloys can comprise in the range of about 2 to 50, 6 to 30, or 12 to 20 weight percent of molybdenum.

In certain embodiments, the amount of nickel, chromium and molybdenum included in the non-noble metal alloys that comprise the conductive layer of electrode, for example, the biosensor component, can vary depending on the specific requirements of the biosensor component as follows: 15 to 34 weight % chromium, 55 to 60 weight % nickel and 7 to 17 weight % molybdenum; or 15 to 17 weight % chromium, 56 to 58 weight nickel and 15 to 17 weight % molybdenum; or 21 to 23 weight % chromium, 54 to 57 weight % nickel and 12 to 14 weight % molybdenum; or 22 to 24 weight % chromium, 58 to 60 weight % nickel 15 to 17 weight % molybdenum; or 32 to 34 weight % chromium, 54 to 57 weight % nickel and 7 to 9 weight molybdenum, all of these weight percentages being based on the total weight percentages of the conductive layer equaling 100 weight percent.

In various embodiments, the non-noble metal alloys of Group I can comprise cobalt. The presence of cobalt in the non-noble metal alloys can comprise, for example, at least about 0.25, 0.5, 1, 1.5, or 2 up to about 10, 8, 6, 5, or 4 weight percent of cobalt. More particularly, the non-noble metal alloys can comprise in the range of about 0 to 10, 1 to 6, or 2 to 4 weight percent of cobalt. It is understood that certain non-noble metal alloys may not contain cobalt.

In various embodiments, the non-noble metal alloys of Group I can comprise iron. The presence of iron in the non-noble metal alloys can comprise, for example, at least about 0.25, 0.5, 2.0, 3.0, or 4 and/or up to about 20, 15, 10, 8, or 6 weight percent of iron. More particularly, the non-noble metal alloys can comprise in the range of about 0 to 20, 1 to 10, or 4 to 6 weight percent of iron.

In various embodiments, the non-noble metal alloys of Group I can comprise tungsten. The presence of tungsten in the non-noble metal alloys can comprise, for example, at least about 0.1, 0.5, 1.0, 2.0, 3.0, or 3.5 and/or up to about 20, 15, 10, 8, or 6 weight percent of tungsten. More particularly, the non-noble metal alloys can comprise in the range of about 0 to 20, 1 to 10, or 3.5 to 6 weight percent of tungsten. It is understood that certain non-noble metal alloys may not contain tungsten.

In various embodiments, the non-noble metal alloys of Group I can comprise manganese. The presence of manganese in the non-noble metal alloys can comprise, for example, at least about 0.1, 0.5, or 1 and/or up to about 5, 4, or 3 weight percent of manganese. More particularly, the non-noble metal alloys can comprise in the range of about 0.1 to 5, 0.5 to 4, or 1 to 3 weight percent of manganese.

In various embodiments, the non-noble metal alloys of Group II can comprise silicon. The presence of silicon in the non-noble metal alloys can comprise, for example, at least about 0.01, 0.1, or 0.5 and/or up to about 2, 1, or 0.8 weight percent of silicon. More particularly, the non-noble metal alloys can comprise in the range of about 0 to 2, 0.1 to 1, or 0.5 to 0.8 weight percent of silicon.

In various embodiments, the non-noble metal alloys of Group II can comprise carbon. The presence of carbon in the non-noble metal alloys can comprise, for example, at least about 0.001 or 0.01 or 0.1 or 0.2 or 0.3 or 0.4 or 0.5 or 0.6 or 0.7 or 0.75 or 0.8 or 0.9 or 1.0 or 1.1 or 1.2 or 1.3 or 1.4 or 1.5 or 1.6 or 1.7 or 1.8 or 1.9 or 2.0 or 0.01 to 0.1 or 0.01 to 0.2 or 0.01 to 0.3 or 0.01 to 0.4 or 0.01 to 0.5 or 0.01 to 0.6 or 0.01 to 0.7 or 0.01 to 0.75 or 0.01 to 0.8 or 0.01 to 0.9 or 0.01 to 1.0 or 0.01 to 1.1 or 0.01 to 1.2 or 0.01 to 1.3 or 0.01 to 1.4 or 0.01 to 1.5 or 0.01 to 1.6 or 0.01 to 1.7 or 0.01 to 1.8 or 0.01 to 1.9 or 0.01 to 2.0 or 0.1 to 0.2 or 0.1 to 0.3 or 0.1 to 0.4 or 0.1 to 0.5 or 0.1 to 0.6 or 0.1 to 0.7 or 0.1 to 0.75 or 0.1 to 0.8 or 0.1 to 0.9 or 0.1 to 1.0 or 0.1 to 1.1 or 0.1 to 1.2 or 0.1 to 1.3 or 0.1 to 1.4 or 0.1 to 1.5 or 0.1 to 1.6 or 0.1 to 1.7 or 0.1 to 1.8 or 0.1 to 1.9 or 0.1 to 2.0 weight percent of carbon.

In various embodiments, the non-noble metal alloys of Group I can comprise copper. The presence of copper in the non-noble metal alloys can comprise, for example, at least about 0.1, 0.5, or 1 and/or up to about 3, 2, or 1.6 weight percent of copper. More particularly, the non-noble metal alloys can comprise in the range of about 0 to 3, 0.5 to 2, or 1 to 1.6 weight percent of copper. It is understood that certain non-noble metal alloys may not contain copper.

In various embodiments, the non-noble metal alloys of Group I can comprise aluminum. The presence of aluminum in the non-noble metal alloys can comprise, for example, at least about 0.01, 0.1, or 0.5 and/or up to about 2, 1, or 0.8 weight percent of aluminum. More particularly, the non-noble metal alloys can comprise in the range of about 0.01 to 2, 0.1 to 1, or 0.5 to 0.8 weight percent of aluminum. It is understood that certain non-noble metal alloys may not contain aluminum.

In various embodiments, the non-noble metal alloys of Group I can comprise titanium. The presence of titanium in the non-noble metal alloys can comprise, for example, at least about 0.001, 0.01, or 0.1 and/or up to about 1, 0.75, or 0.5 weight percent of titanium. More particularly, the non-noble metal alloys can comprise in the range of about 0 to 1, 0.01 to 0.75, or 0.1 to 0.5 weight percent of titanium. It is understood that certain non-noble metal alloys may not contain aluminum.

In various embodiments, the non-noble metal alloys of Group I can comprise boron. The presence of boron in the non-noble metal alloys can comprise, for example, at least about 0.0001, 0.001, or 0.005 and/or up to about 0.1, 0.01, or 0.008 weight percent of boron. More particularly, the non-noble metal alloys can comprise in the range of about 0 to 0.1, 0.001 to 0.01, or 0.005 to 0.008 weight percent of boron. It is understood that certain non-noble metal alloys may not contain boron.

In various embodiments, the non-noble metal alloys of Group I can comprise vanadium. The presence of vanadium in the non-noble metal alloys can comprise, for example, at least about 0.001, 0.01, or 0.1 and/or up to about 1, 0.75, or 0.5 weight percent of vanadium. More particularly, the non-noble metal alloys can comprise in the range of about 0 to 1, 0.01 to 0.75, or 0.1 to 0.5 weight percent of vanadium. It is understood that certain non-noble metal alloys may not contain vanadium.

In certain specific embodiments, such as Compositions A3-A6 of Table 1, the non-noble metal alloys may comprise nickel and chromium, with a combined weight percent of the nickel and chromium in the range of 50 to 99 weight percent. The non-noble metal alloys may particularly comprise nickel having a weight percent in the range of 55 to 60 weight percent, chromium having a weight percent in the range of 15 to 34 weight percent, and molybdenum having a weight percent in the range of 7 to 17 weight percent. The non-noble metal alloys may also comprise cobalt having a weight percent in the range of 0 to 4 weight percent, iron having a weight percent in the range of 0 to 6 weight percent, tungsten having a weight percent in the range of 0 to 5 weight percent, manganese having a weight percent in the range of 0 to 2 weight percent, silicon having a weight percent in the range of 0 to 1 weight percent, carbon having a weight percent in the range of 0 to 0.10 weight percent, copper having a weight percent in the range of 0 to 2 weight percent, aluminum having a weight percent in the range of 0 to 1 weight percent, and vanadium having a weight percent in the range of 0 to 1 weight percent.

In certain specific embodiments, such as Composition A3 of Table 1, the non-noble metal alloys may comprise nickel and chromium, with a combined weight percent of the nickel and chromium in the range of 50 to 99 weight percent. The non-noble metal alloys may particularly comprise nickel having a weight percent in the range of 56 to 58 weight percent, chromium having a weight percent in the range of 15 and 17 weight percent, and molybdenum having a weight percent in the range of 15 to 17 weight percent. The non-noble metal alloys may also comprise cobalt having a weight percent in the range of 0 to 4 weight percent, iron having a weight percent in the range of 4 to 6 weight percent, tungsten having a weight percent in the range of 3 to 5 weight percent, manganese having a weight percent in the range of 0 to 2 weight percent, silicon having a weight percent in the range of 0 to 0.10 weight percent, carbon having a weight percent in the range of 0 to 0.10 weight percent, and vanadium having a weight percent in the range of 0 to 1 weight percent.

In certain specific embodiments, such Composition A4 of Table 1, the non-noble metal alloys may comprise nickel and chromium, with a combined weight percent of the nickel and chromium in the range of 50 to 99 weight percent. The non-noble metal alloys may particularly comprise nickel having a weight percent in the range of 54 to 57 weight percent, chromium having a weight percent in the range of 21 to 23 weight percent, and molybdenum having a weight percent in the range of 12 to 14 weight percent. The non-noble metal alloys may also comprise cobalt having a weight percent in the range of 0 to 4 weight percent, iron having a weight percent in the range of 2 to 4 weight percent, tungsten having a weight percent of 2 to 4 weight percent, manganese having a weight percent in the range of 0 to 1 weight percent, silicon having a weight percent in the range of 0 to 0.10 weight percent, carbon having a weight percent in the range of 0 to 0.010 weight percent, and vanadium having a weight percent in the range of 0 to 1 weight percent.

In certain specific embodiments, such as Composition A5 of Table 1, the non-noble metal alloys may comprise nickel and chromium, with a combined weight percent of the nickel and chromium in the range of 50 to 99 weight percent. The non-noble metal alloys may particularly comprise nickel having a weight percent in the range of 58 to 60 weight percent, chromium having a weight percent in the range of 22 to 24 weight percent, and molybdenum having a weight percent in the range of 15 to 17 weight percent. The non-noble metal alloys may also comprise cobalt having a weight percent in the range of 0 to 3 weight percent, iron having a weight percent in the range of 0 to 4 weight percent, manganese having a weight percent in the range of 0 to 1 weight percent, silicon having a weight percent in the range of 0 to 0.10 weight percent, carbon having a weight percent in the range of 0 to 0.10 weight percent, and copper having a weight percent in the range of 0.5 to 3 weight percent.

In certain specific embodiments, such as Composition A6 of Table 1, the non-noble metal alloys may comprise nickel and chromium, with a combined weight percent of the nickel and chromium in the range of 50 to 99 weight percent. The non-noble metal alloys may particularly comprise nickel having a weight percent in the range of 54 to 57 weight percent, chromium having a weight percent in the range of 32 to 34 weight percent, and molybdenum having a weight percent in the range of 7 to 9 weight percent. The non-noble metal alloys may also comprise iron having a weight percent in the range of 0 to 3 weight percent, manganese having a weight percent in the range of 0 to 1 weight percent, silicon having a weight percent in the range of 0 to 1 weight percent, carbon having a weight percent in the range of 0 to 0.10 weight percent, and aluminum having a weight percent in the range of 0 to 1 weight percent.

Conductive layers in the present disclosure can be constructed of a single layer comprising any of the alloy compositions disclosed in this application. In certain embodiments, the alloy composition contains an alloy which can be a solid solution of the elements (a single phase), a mixture of metallic phases (two or more solutions) or an intermetallic compound with no distinct boundary between the phases.

As one skilled in the art would readily appreciate, the elements of the non-noble metal alloys may comprise incidental impurities. As used herein, "incidental impurities" refer to any impurities that naturally occur in the ore used to the produce the non-noble metal alloys or that are inadvertently added during the production process. The non-noble metal alloys can comprise less than about 0.1, 0.05, or 0.001 weight percent of the incidental impurities.

The non-noble metal alloys described herein may also contain one or more additional alloying elements, which are in addition to the elements described above. However, in various embodiments, the non-noble metal alloys can be substantially free from such additional alloying elements. As used herein, the terms "practically free" and "substantially free" mean that the non-noble metal alloy comprises less than 0.001 weight percent of such additional alloying components. Furthermore, the terms "practically free" and "substantially free" may be used interchangeably.

In certain embodiments of the present disclosure, the biosensor components described herein can be prepared by performing the following steps:
(a) providing a substrate;
(b) providing a target; and
(c) physical vapor depositing at least a portion of the substrate with material from the target to thereby form a conductive layer on the substrate.

The providing a substrate of step (a) may include the provision of any type of substrate material, such as PET, as was previously described. In certain embodiments, the substrate will comprise a sheet of substrate material that can be actuated within a high vacuum chamber. The sheet of substrate material may comprise a single section of material, such as a square sheet. In some other embodiments, sheet of substrate material may comprise a roll of material that is passed, via a roll-to-roll mechanism, through the high vacuum chamber, as will be described in more detail below. In other embodiments, the substrate may be held stationary or may be rotated during deposition, as will be also described below.

The providing a target of step (b) may include the provision of a physical vapor deposition target comprised of any of the non-noble metal alloys previously described. For example, in some embodiments, the physical vapor deposition target may comprise one of the alloys comprising one of the Compositions A1-A6 listed in Table 1. Such alloy targets may comprise less than about 0.1, 0.05, or 0.001 weight percent of incidental impurities. In some embodiments, the physical vapor deposition target will be housed within and/or will comprise an electrode, such as a sputter cathode, during the physical vapor deposition process. In certain embodiments, the physical vapor deposition target may be a circular, having a diameter of at least 2, 4, 8, 12, 16, or 20 cm. In other embodiments, the physical vapor deposition target may be a tubular target having an inner diameter of at least 2, 4, 8, or 16 cm and an outer diameter of 20, 24, 28 or 32 cm. In still other embodiments, the physical vapor deposition target may be rectangular with dimensions of: a width of between 5 to 25 cm, a length of between 25 to 75 cm, and a thickness of between 0.3 to 5 cm. It should be understood, however, that embodiments of the present disclosure contemplate the use of other-shaped and sized targets.

The physical vapor depositing of step (c) generally includes the coating of the substrate with the material from the non-noble metal alloy target to form the conductive layer. As used herein, the term "physical vapor deposition" shall denote depositing thin-films by providing for the condensation of vaporized material onto a substrate. The physical vapor deposited coating may be performed with any type of physical vapor deposition process previously described, i.e., sputter coating, thermal evaporation, electron beam evaporation, laser ablation, arc vaporization, co-evaporation, ion plating, or the like. For example, in some embodiments, the physical vapor depositing step will be performed via a sputtering process, in which the substrate is coated with the conductive layer by sputtering the non-noble metal alloy target via the sputtering device. Specific examples of such a sputtering-type physical vapor depositing will be described in more detail below. The resulting substrate with the conductive layer coated thereon may be used as a biosensor component, such as an electrode. Such electrodes may include a working electrode, a reference electrode, or a counter electrode. In certain embodiments, such as when a roll of substrate material is vacuum coated with a conductive layer, via a roll-to-roll physical vapor deposition process, the resulting thin-film sheet may be cut apart to appropriate size to form a thin-film electrode specifically sized for the biosensor component. In other embodiments, the biosensor components can be formed from the thin-film sheet by etching, such as chemical or laser etching. In still other embodiments, the biosensor components can be formed using a patterned mask, which is laid on the substrate, and the conductive layer is physical vapor deposited thereover to form the biosensor component.

In certain specific embodiments, the biosensor components may be created via a roll-to-roll physical vapor deposition process that includes roll-to-roll magnetron sputtering. For instance, a substrate sheet comprising a polymer film made of PET (polyethyleneptrapthalate) with a thickness ranging from 25 µm to 250 µm and width of 33.02 cm may be sputtered using a 77.50 cm wide web roll-to-roll magnetron sputter coater, such as a the Smartweb coater offered by Applied Materials, Inc. or the Mark 80 offered by CHA Industries, Inc. A single or a dual target configuration can be employed to deposit a conductive layer of non-noble metal alloys, such as those alloys from Table 1. A target comprised of a non-noble metal alloy plate (such as is available from Tricor Industries Inc.) can be used. A vacuum chamber of the sputter coater can be pumped down to base pressure of at least $10^{-5}$ Torr using a diffusion and mechanical pump combination. In other embodiments a combination of a mechanical pump, a turbo pump, a cryo pump, and/or an oil diffusion pump may be used. Magnetron sputtering cathodes housing the non-noble metal alloy targets having a generally rectangular shape of 15.24 cm×30.48 cm can be energized using 2 KW power supplies (such as offered from Advanced Energy Inc.). An argon gas flow into the vacuum chamber can be controlled (such as via a MKS model 1179A flow controller) to set a sputtering pressure between 3 to 10 mTorr for use during the sputtering process.

A thickness and sheet resistance of the sputtered conductive layer can be efficiently controlled in-situ by controlling the roll-to-roll web speeds, i.e., controlling the speed of the substrate sheet as it travels through the vacuum chamber during sputtering. For example, for sputtering of a conductive layer of Composition A3, the web speed can be set to between 0.1 to 3.5 meters per minute and sputtering power density of between 2 to 8 Watts per square cm. As such, sputtered conductive layer of Composition A3 may be formed having a measured thickness value of about 25 nm and a sheet resistance of about 45 ohms per square.

In addition to the roll-to-roll process described above, biosensor components can be manufacture using a scaled-up version of the same geometry, using a large-scale roll-to-roll process. In such a large-scale roll-to-roll process, maximum web speeds can be 0.1 to 10 meters per minute, between 3 to 7 meters per minute, or higher than 10 meters per minute. The large-scale roll-to-roll process may provide a sputtering power density between 0.1 to 13, 2 to 10, or 5 to 8 Watts per square cm. Additionally, the number of targets can include between 2, 4, 6 or more, and the web width of the substrate sheet can be from 75 cm or larger.

Embodiments additionally contemplate that physical vapor deposition processes can be utilized in which substrate sheets are held stationary within the vacuum chamber. Certain of such embodiments, are described in detail below in the Examples section. In some embodiments in which the substrate sheets are held stationary, deposition times for depositing the conductive layer on the substrate sheets may be 5, 10, 15, 30 minutes or more.

As previously noted above, biosensor components that include conductive layer formed from the non-noble metal alloys described herein can exhibit desirable electrochemical properties that make them particularly well suited as replacements for biosensor components that incorporate noble metals, such as palladium and/or gold. For instance, the biosensor components of embodiments of the present disclosure may comprise a thin-film electrode formed with a non-noble metal alloy conductive layer that exhibits desirable dose-response characteristics when undergoing chronoamperometry tests. In particular, when undergoing a chronoamperometry test defined by the Type 1 Chronoamperometry Test described below, the thin-film electrode of the present disclosure may have a dose-response slope that deviates from a dose-response slope of a palladium-based thin-film electrode by no more than 20%, 19%, 18%, 17%, 16%, 15%, 14%, 13%, 12%, 11%, 10%, 9%, 8%, or 7%. In certain specific embodiments, the dose-response slope of the thin-film electrode of the present disclosure may deviate from the dose-response slope of a palladium-based thin-film electrode between 15 to 7%, 14 to 8%, 13 to 9%, or 12 to 10%.

In various embodiments, the biosensor component will comprise a thin-film electrode formed with the non-noble metal alloy conductive layer that alternatively, or in addition, exhibits desirable electron transfer kinetics when undergoing chronoamperometry tests. For instance, when undergoing a Linear Sweep Voltammetry test as defined in the Type 1 Linear Sweep Voltammetry Test described below, the thin-film electrode is operable to generate a current of less than 0.5 µA while having a potential step of −100, −60, 0, 50, 100, 150, 200, 250, or 300 mV applied to the thin-film electrode. In certain specific embodiments, the thin-film electrode is operable to generate a current of less than 0.5 µA while having a potential step of between −100 to 0, 0 to 100, 100 to 200, 200 to 300, or 300-400 mV, as measured versus a saturated calomel reference electrode of the Type 1 Linear Sweep Voltammetry Test, applied to the thin-film electrode.

This invention can be further illustrated by the following examples of embodiments thereof, although it will be understood that these examples are included merely for the purposes of illustration and are not intended to limit the scope of the invention unless otherwise specifically indicated.

EXAMPLES

Preparation of Thin-Film Electrodes

For each of the below-described examples, biosensor components in the form of thin-film electrodes were formed by the following-described physical vapor deposition process. It is understood that thin-film electrodes can be formed, using the below process, to include a conductive layer of a plurality of different types of metals and metal alloys, such as the non-noble metal alloys listed in Table 1, as well as noble metals, such as palladium and gold. The process included forming thin-film electrode films by:
  (a) metal or metal alloys were deposited on 10.16 cm×10.16 cm square PET substrate sheet using direct current ("DC") magnetron sputtering in a high vacuum chamber, with the sputtering having been performed with a Denton Vacuum Desktop Pro sputtering device;
  (b) the vacuum chamber was evacuated to an initial base pressure of −10-5 mTorr;
  (c) argon gas of 10 sccm was introduced into the high vacuum chamber to create a deposition pressure of 2.8 mTorr;
  (d) the substrate sheets were rotated at approximately two revolutions per minute within the vacuum chamber;
  (e) a 5.08 cm diameter target of the metal or metal alloys was held at a constant power of 40 Watts under the DC magnetron sputtering device for deposition time of 15 minutes to coat at least a portion of the substrate sheet with the conductive layer (to initialize the targets, the targets were held at a constant power of 40 Watts under the DC magnetron sputtering device for a 5 minute pre-sputtering time prior to the substrates being introduced into the vacuum chamber); and
  (f) all depositions were carried out at room temperature.

Individual thin-film electrodes, with a size of 5.08 cm×7.62 cm, were cut from the thin-film electrode films that were formed by physical vapor deposition, as provided above. Electrochemical experiments were conducted using a Gamry Instruments Reference 600 potentiostat in a three-electrode configuration, with the electrochemical cell containing the thin-film electrode film positioned inside of a Gamry Instruments VistaShield Faraday Cage. Each of the thin-film electrodes was formed as a working electrode by partially masking the thin-film electrode with electroplating tape having a single 3 mm diameter aperture die-cut into it. As such, an unmasked portion of the thin-film electrode provided a geometric working electrode surface area of 0.0707 square cm. The unmasked portion of the thin-film electrode served as an electrical connection point to a working electrode lead of the potentiostat. The masked portion of the thin-film electrode was placed onto a flat supporting block of non-conductive material, such as plastic. The thin-film electrode was thereafter placed into a working electrode port of a glass electrochemical cell. The exposed 3 mm diameter portion of the thin-film electrode was positioned near a center of a bottom opening of working electrode port of the electrochemical cell. The working electrode port of the electrochemical cell was sealed with a clamp and an O-ring. The electrochemical cell also contained a reference electrode comprising a saturated calomel reference electrode and a carbon auxiliary electrode. The reference electrode and the auxiliary electrode were placed, respectively in a reference electrode port and an auxiliary electrode portion. Additionally, the reference electrode and the auxiliary electrode were connected, respectively, to a reference lead and an auxiliary lead of the potentiostat. The electrochemical cell also included a gas flow port by which to deaerate and blanket test solutions with inert gas, such as nitrogen.

Description of Type 1 Chronoamperometry Test

Certain of the examples to follow were performed using the Type 1 Chronoamperometry Test, which is defined as follows: 50 mL of 20 mM N-tris(hydroxymethyl)methyl-2-aminoethanesulfonic acid buffer solution at pH 7.1 was placed into the electrochemical cell and the electrochemical cell was sealed with stoppers. Gas inlet and outlet fittings, which were associated with the gas flow port, allowed inert gas sparging (i.e., de-aerating) of the buffer solution, via a gas flow of nitrogen, using a medium-porous filter stick. The gas flow port additionally allowed the gas flow to be switched from the filter stick to a headspace-blanketing arrangement. The gas outlet was connected to an oil bubbler to prevent back-diffusion of external gas (e.g., air) into the electrochemical cell.

An amount of ruthenium (II) hexamine chloride (i.e., $Ru(NH_3)_6Cl_2$ or the "mediator") was prepared in situ and added to the de-aerated buffer solution. In particular, an appropriate mass of mediator was measured and added to the buffer solution to achieve a desired mediator concentration in the buffer solution. The mass of mediator was added to the electrochemical cell through a normally-stoppered ground glass joint while the headspace was being blanketed with nitrogen. After the addition of the appropriate mediator amount, a stopper was used to seal the cell and a magnetic stirbar was used to stir the resulting solution (the "mediator solution") for 5 minutes before an electrochemical experiment was performed. After addition of the mediator to the buffer solution, no agitation of the mediator solution from sparging or otherwise was performed during the Type 1 Chronoamperometry Test (i.e., the solution was quiescent during electrochemical testing).

Figure 3:
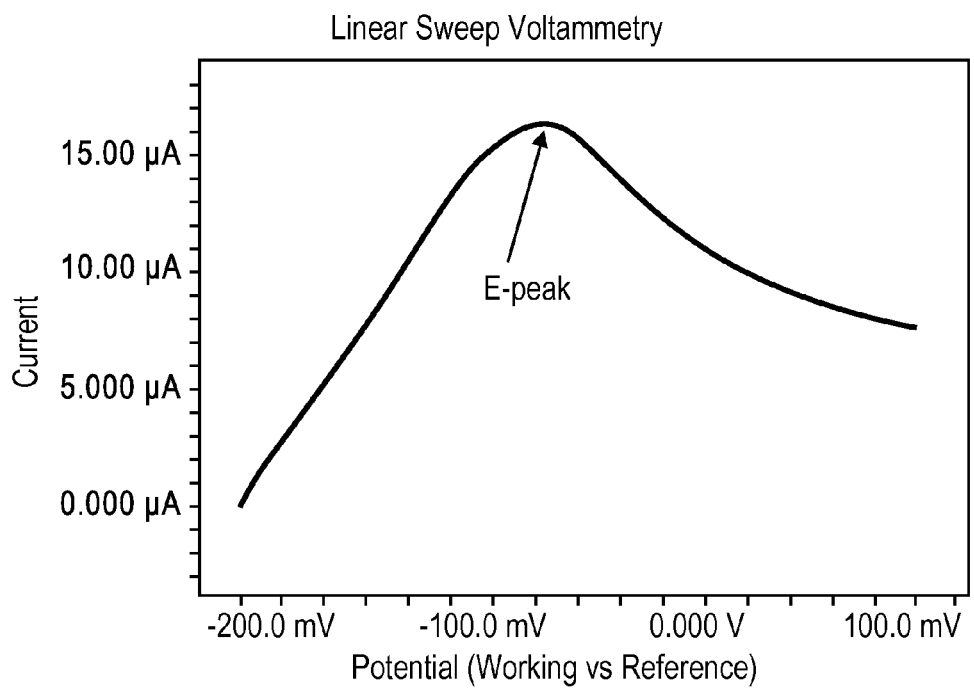
FIG. 3 is a graph depicting a linear sweep voltammogram plot of a thin-film electrode in a mediator-containing solution.

An anodic linear sweep voltammogram was performed at a scan rate of 25 mV per second to obtain an oxidation wave of the mediator at the thin-film electrode. From the voltammogram, a peak voltage ("E-peak") of the oxidation wave was determined, with such E-peak being defined as the voltage at which the peak current flows, as measured between the working electrode and the counter electrode versus the reference electrode. An illustration of an oxidation wave and an associated E-peak, as obtained from a thin-film electrode formed with a palladium conductive layer, are illustrated in FIG. 3. As can be seen from FIG. 3, the measured E-peak value was approximately −76 mV, as measured versus the saturated calomel reference electrode.

Figure 4:
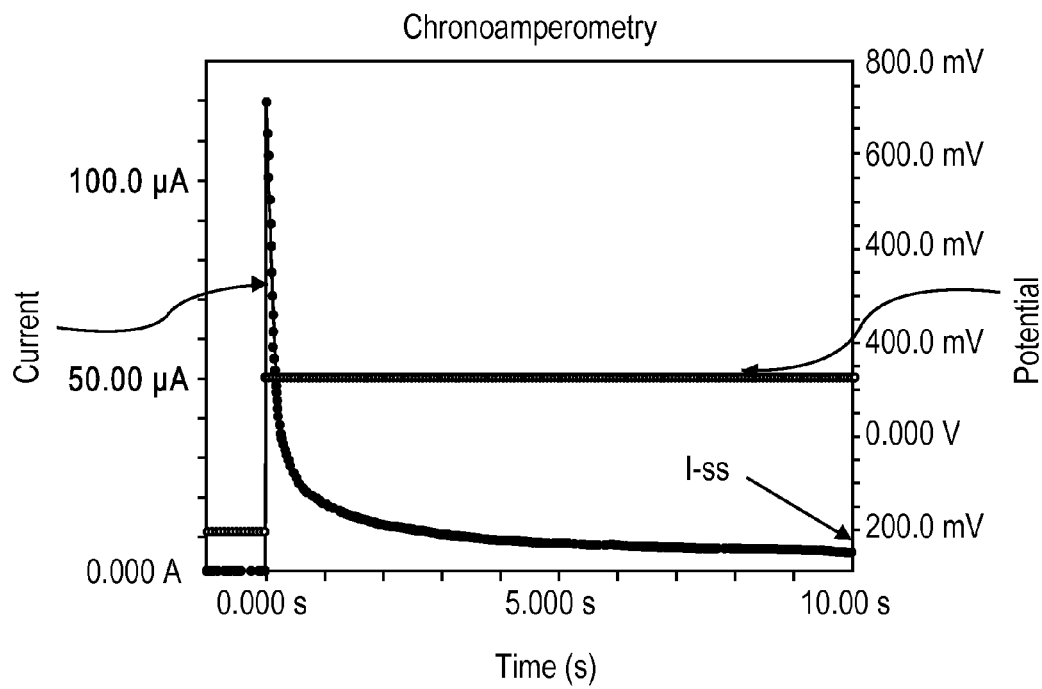
FIG. 4 is a graph depicting a chronoamperometry plot of the thin-film electrode in the mediator-containing solution from FIG. 3.

Next, the thin-film electrode was evaluated by chronoamperometry by applying a potential step of +200 mV versus E-peak (i.e., 200 mV more anodic than E-peak) to the thin-film electrode after a 1 second delay while the thin-film electrode was held at the rest potential, with all potentials measured between the working electrode and the reference electrode. The applied potential of +200 mV versus E-peak was chosen so that the resulting current was controlled by mass transport of the mediator. The resulting electrochemical current at the thin-film electrode was recorded at a sample rate of 100 Hz for at least 10 seconds after the potential step was applied. The electrochemical current value measured at 10 seconds after the potential step was applied was determined as I-ss (steady state current at 10 seconds). An illustration of the electrochemical current of a thin-film electrode formed with a palladium conductive layer, recorded for 10 seconds and including the I-ss value (steady state current at 10 seconds), is illustrated in FIG. 4.

Thereafter, additional amounts of mediator were added to the mediator solution to increase the concentration of the mediator. Upon successive additions of mediator, additional voltammograms were performed for each concentration of mediator, such that an E-peak was determined for each oxidation wave obtained for each mediator concentration.

Correspondingly, chronoamperometry was performed for each concentration of mediator by applying a potential step of +200 mV versus the determined E-peak. For the Type 1 Chronoamperometry Test, at least five different E-peak and corresponding I-ss values were determined, with each E-peak and corresponding I-ss value being associated with a given mediator concentration.

Figure 5:
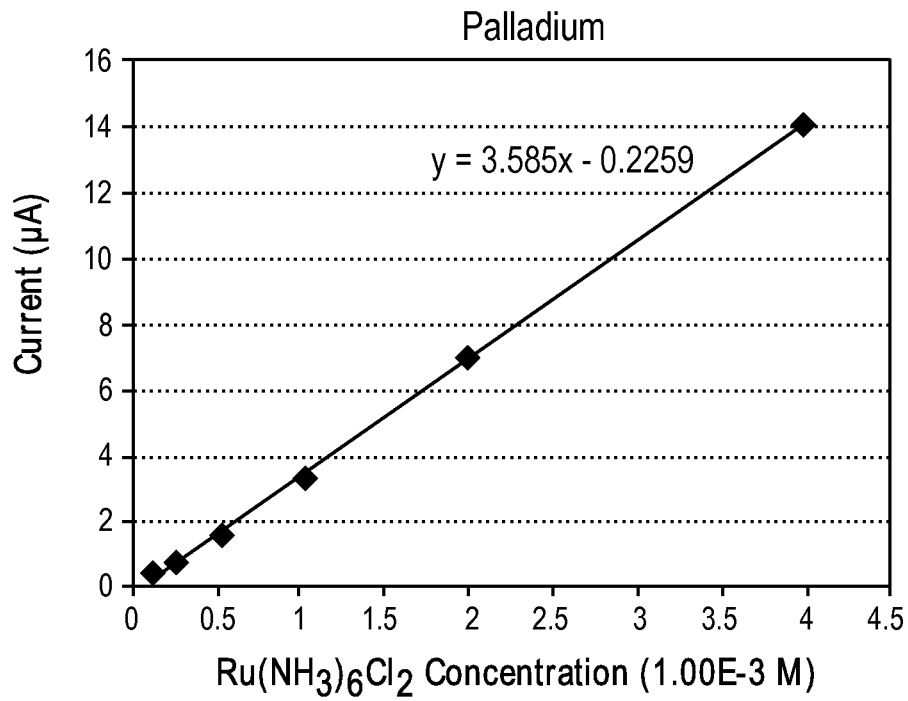
FIG. 5 is a graph depicting a dose-response slope of a thin-film electrode having a conductive layer formed from palladium.

Next, each of the five or more measured I-ss values were plotted on a graph as a function of ruthenium (II) hexamine chloride concentration. For each these plots, a linear regression was performed on the plotted I-ss values so as to determine a linear equation that fit the plotted I-ss values. A linear slope was calculated from the linear equation, and such linear slope was used as a dose-response characteristic of the thin-film electrode under experiment. Such a slope value (i.e., dose-response) results in a value of current per mediator concentration. FIG. 5 is illustrative of I-ss values and a linear fit obtained via linear regression for a thin-film electrode formed with a palladium conductive layer. The linear slope can be obtained from the linear regression. The linear slope demonstrates how the thin-film electrode, and specifically the electrochemical response (i.e., dose-response) of the thin-film electrode, behaves with varying mediator concentration.

Application of Type 1 Chronoamperometry Test to Thin-Film Electrodes

Two exemplary series of experiments were performed, whereby multiple thin-film electrodes where tested under the Type 1 Chronoamperometry Test and the dose-response slope of each thin-film electrode in a given series was compared with the other dose-response slopes of the thin-film electrodes in the given series. In the first series, a thin-film electrode with a palladium conductive layer and a thin-film electrode with a Composition A3 conductive layer were tested under the Type 1 Chronoamperometry Test, and their dose-response slopes were compared. In the second series, a first thin-film electrode with a palladium conductive layer, a second thin-film electrode with a palladium conductive layer and a thin-film electrode with a Composition A3 conductive layer were tested under the Type 1 Chronoamperometry Test, and their dose-response slopes were compared.

For each of the exemplary first and second series, six and five, respectively, different concentrations of ruthenium (II) hexamine chloride mediator where added to the buffer solution. The targeted mediator concentrations (in molar), targeted mediator mass to add to the buffer solution (in grams), actual mediator mass added to the buffer solution (in grams), cumulative total mediator mass added to the buffer solution (in grams), cumulative, actual mediator concentration for the resulting mediator solution (in molar), and I-ss values determined for each mediator concentration for the thin-film electrode formed with the palladium conductive layer from the exemplary first series is shown below in Table 2. Corresponding values for the thin-film electrode formed with the Composition A3 conductive layer from the exemplary first series are shown in Tables 3 and 4, respectively. Similarly, corresponding values for the first thin-film electrode formed with the palladium conductive layer, the second thin-film electrode formed with the palladium conductive layer, and the thin-film electrode formed with the Composition A3 conductive layer, each from the exemplary second series, are shown in Tables 4, 5, and 6, respectively.

TABLE 2

Thin-film Electrode with Palladium Conductive Layer - First Exemplary Series

| Target Concentration (M) | Target Mass to Add (g) | Actual Mass Added (g) | Cumulative Total Mass (g) | Actual Concentration (M) | I-ss (µA) |
|---|---|---|---|---|---|
| 1.25E−04 | 0.001714 | 0.001788 | 0.001788 | 1.30E−04 | 0.439 |
| 2.50E−04 | 0.001714 | 0.001754 | 0.003542 | 2.58E−04 | 0.665 |
| 5.00E−04 | 0.003428 | 0.003596 | 0.007138 | 5.21E−04 | 1.522 |
| 1.00E−03 | 0.006855 | 0.006846 | 0.013984 | 1.02E−03 | 3.301 |
| 2.00E−03 | 0.013711 | 0.013323 | 0.027307 | 1.99E−03 | 6.997 |
| 4.00E−03 | 0.027421 | 0.027278 | 0.054585 | 3.98E−03 | 14.05 |

TABLE 3

Thin-film Electrode with Composition A3 Conductive Layer - First Exemplary Series

| Target Concentration (M) | Target Mass to Add (g) | Actual Mass Added (g) | Cumulative Total Mass (g) | Actual Concentration (M) | I-ss (µA) |
|---|---|---|---|---|---|
| 1.25E−04 | 0.001714 | 0.001798 | 0.001798 | 1.31E−04 | 0.4 |
| 2.50E−04 | 0.001714 | 0.001773 | 0.003571 | 2.60E−04 | 0.562 |
| 5.00E−04 | 0.003428 | 0.003445 | 0.007016 | 5.12E−04 | 1.297 |
| 1.00E−03 | 0.006855 | 0.006895 | 0.013911 | 1.02E−03 | 3.016 |
| 2.00E−03 | 0.013711 | 0.013861 | 0.027772 | 2.03E−03 | 6.708 |
| 4.00E−03 | 0.027421 | 0.027473 | 0.055245 | 4.03E−03 | 13.7 |

TABLE 4

Thin-film Electrode with Palladium #1 Conductive Layer - Second Exemplary Series

| Target Concentration (M) | Target Mass to Add (g) | Actual Mass Added (g) | Cumulative Total Mass (g) | Actual Concentration (M) | I-ss (µA) |
|---|---|---|---|---|---|
| 1.25E−04 | 0.001714 | 0.001853 | 0.001853 | 1.35E−04 | 0.3535 |
| 2.50E−04 | 0.001714 | 0.001727 | 0.00358 | 2.61E−04 | 0.7345 |
| 5.00E−04 | 0.003428 | 0.003407 | 0.006987 | 5.10E−04 | 1.457 |
| 1.00E−03 | 0.006855 | 0.006896 | 0.013883 | 1.01E−03 | 2.6155 |
| 2.00E−03 | 0.013711 | 0.013753 | 0.027636 | 2.02E−03 | 5.9945 |

TABLE 5

Thin-film Electrode with Palladium #2 Conductive Layer - Second Exemplary Series

| Target Concentration (M) | Target Mass to Add (g) | Actual Mass Added (g) | Cumulative Total Mass (g) | Actual Concentration (M) | I-ss (µA) |
|---|---|---|---|---|---|
| 1.25E−04 | 0.001714 | 0.001897 | 0.001897 | 1.38E−04 | 0.23165 |
| 2.50E−04 | 0.001714 | 0.001814 | 0.003711 | 2.71E−04 | 0.694 |
| 5.00E−04 | 0.003428 | 0.00354 | 0.007251 | 5.29E−04 | 1.2165 |
| 1.00E−03 | 0.006855 | 0.00688 | 0.014131 | 1.03E−03 | 2.964 |
| 2.00E−03 | 0.013711 | 0.013681 | 0.027812 | 2.03E−03 | 5.4865 |

TABLE 6

Thin-film Electrode with Composition A3 Conductive Layer - Second Exemplary Series

| Target Concentration (M) | Target Mass to Add (g) | Actual Mass Added (g) | Cumulative Total Mass (g) | Actual Concentration (M) | I-ss (μA) |
|---|---|---|---|---|---|
| 1.25E−04 | 0.001714 | 0.001657 | 0.001657 | 1.21E−04 | 0.414 |
| 2.50E−04 | 0.001714 | 0.001682 | 0.003339 | 2.44E−04 | 0.6975 |
| 5.00E−04 | 0.003428 | 0.003457 | 0.006796 | 4.96E−04 | 1.42 |
| 1.00E−03 | 0.006855 | 0.007072 | 0.013868 | 1.01E−03 | 3.0785 |
| 2.00E−03 | 0.013711 | 0.013967 | 0.027835 | 2.03E−03 | 6.4225 |

Figure 6:
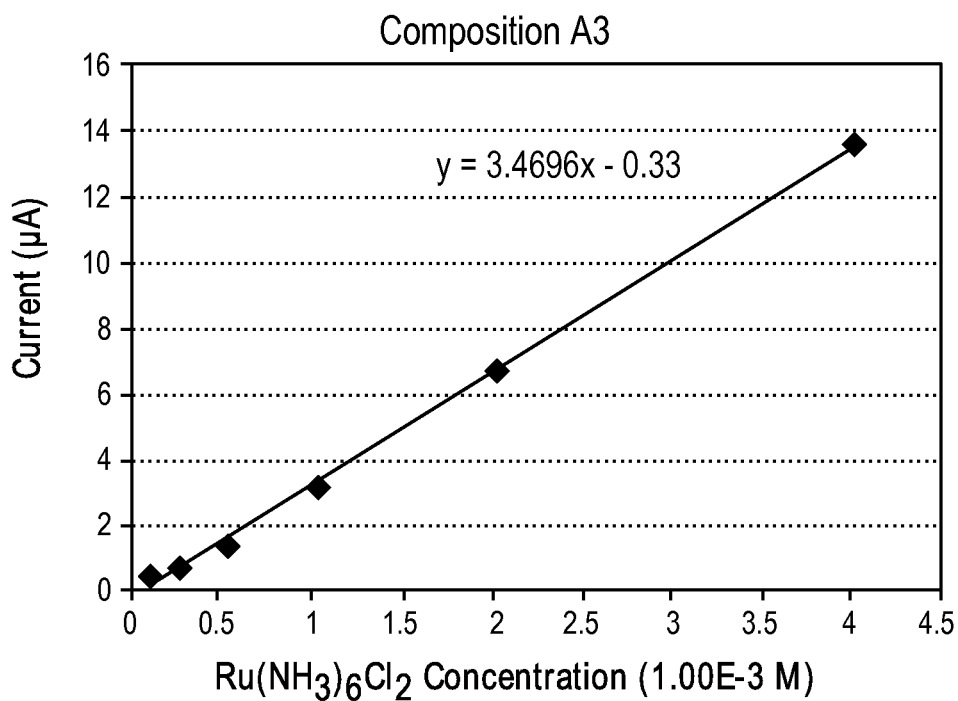
FIG. 6 is a graph depicting a dose-response slope of a thin-film electrode having a conductive layer formed from a Composition A3.
Figure 7:
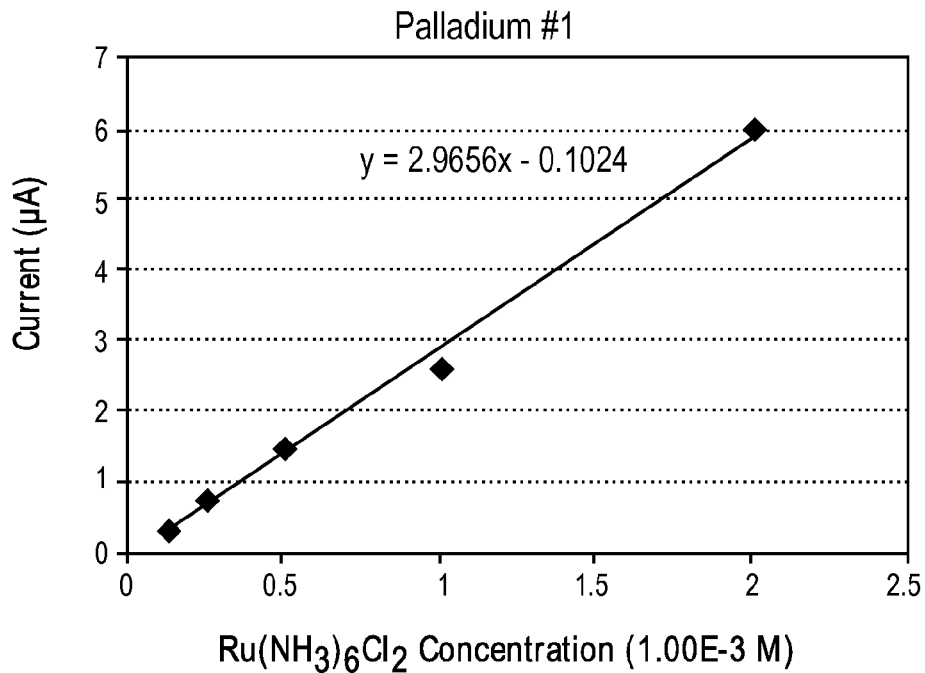
FIG. 7 is a graph depicting another dose-response slope of a thin-film electrode having a conductive layer formed from palladium.
Figure 8:
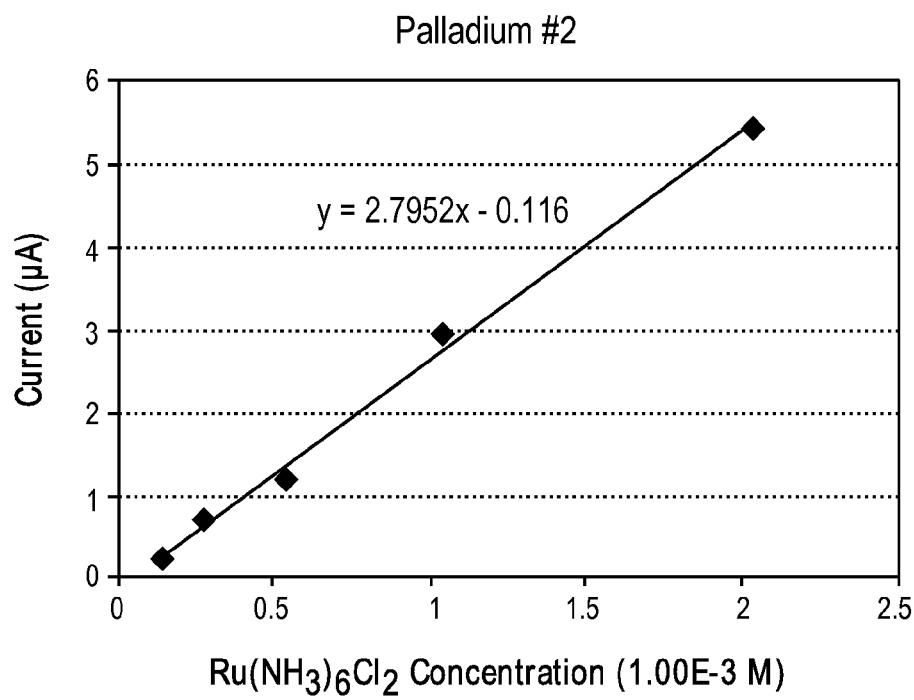
FIG. 8 is a graph depicting still another dose-response slope of a thin-film electrode having a conductive layer formed from palladium.
Figure 9:
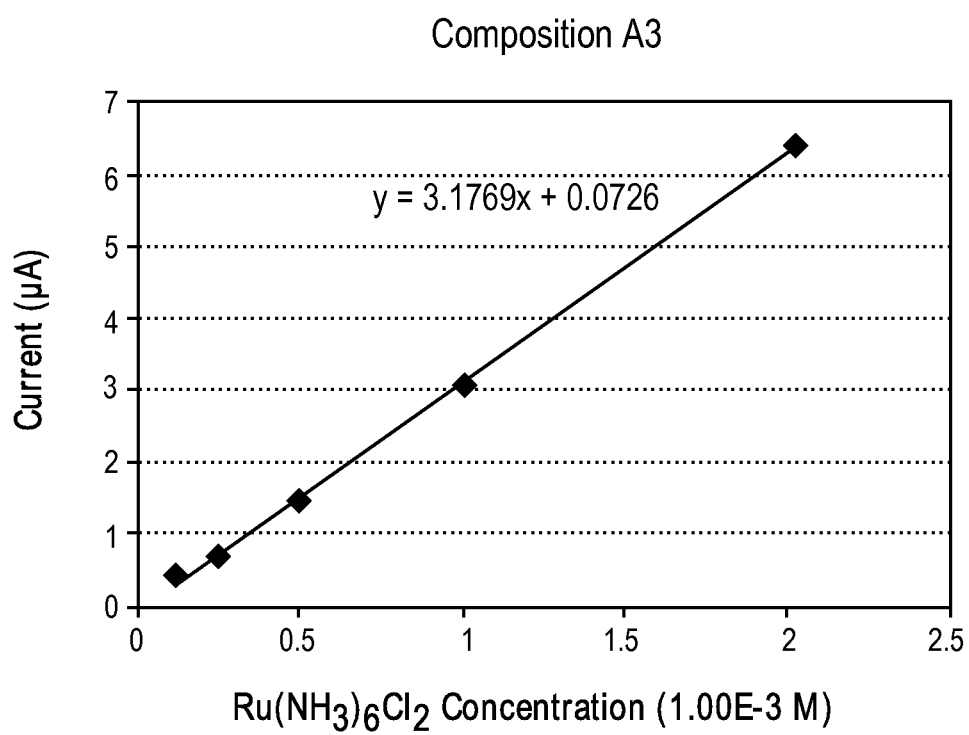
FIG. 9 is a graph depicting another dose-response slope of a thin-film electrode having a conductive layer formed from Composition A3.

For each of the thin-film electrodes in the first and second exemplary series, the electrochemical current I-ss was recorded at 10 seconds for each mediator (i.e., ruthenium hexamine) concentration. Such I-ss values are also illustrated in Tables 2-6. Next, the I-ss values for each thin-film electrode were plotted graphically as a function of the mediator concentration. For example, FIGS. 5-6 illustrate the electrochemical currents recorded at 10 seconds as a function of the mediator concentration for each of the thin-film electrodes included within the first exemplary series, i.e., the thin-film electrode formed with a palladium conductive layer (i.e., FIG. 5), and the thin-film electrode formed with the Composition A3 conductive layer (i.e., FIG. 6). For each these plots, a linear regression was performed on the plotted I-ss values so as to determine a linear equation that fit the plotted I-ss values. Linear slopes were calculated from the linear equations, and such linear slopes were used as dose-response characteristics of the thin-film electrodes in current per millimolar mediator. Such linear slopes (i.e., dose-response slopes) were likewise obtained for the thin-film electrodes in the exemplary second series. For example, FIGS. 7-9 illustrate the electrochemical currents recorded at 10 seconds as a function of the mediator concentration for each of the thin-film electrodes included within the second exemplary series, i.e., the first thin-film electrode formed with a palladium conductive layer (i.e., FIG. 7), the second thin-film electrode formed with a palladium conductive layer (i.e., FIG. 8) and the thin-film electrode formed with the Composition A3 conductive layer (i.e., FIG. 9).

To simplify a comparison of the dose-responses amongst the thin-film electrodes within each of the first and second series, the dose-response slopes were normalized. In more detail, the dose-response slopes for each of the thin-film electrodes within the first series was normalized with respect to the dose-responses slope of the thin-film electrode formed with the palladium conductive layer. Similarly, the dose-response slopes for each of the thin-film electrodes within the second series were normalized with respect to the dose-response slope of the first thin-film electrode formed with the palladium conductive layer. Specifically, for each of the exemplary series, the dose-response slopes of each of the thin-film electrodes were normalized (i.e., mathematically divided) by the dose-response slope of the thin-film electrode form with a palladium conductive layer. As a result, the normalized dose-response slope of the thin-film electrode form with a palladium conductive layer in the first series was one (i.e., mathematical unity). Similarly, the normalized dose-response slope of the first thin-film electrode form with a palladium conductive layer in the second series was one (i.e., mathematical unity).

Table 7 below illustrates the normalized dose-response slopes of each of the thin-film electrodes in both of the first and second exemplary series. Contrastingly, the thin-film electrode formed with the Composition A3 conductive layer was found to deviate less than 4% from that of the thin-film electrode formed with the palladium conductive layer.

TABLE 7

| Thin-film Electrode | Dose-response Slope Normalized to Palladium #1 First Exemplary Series | Dose-response Slope Normalized to Palladium #1 Second Exemplary Series |
|---|---|---|
| Palladium #1 | 1 | 1 |
| Palladium #2 | — | 0.9436 |
| Composition A3 | 0.968 | 1.0737 |

In the second exemplary series, when compared to the dose-response slope obtained for the first thin-film electrode formed with the palladium conductive layer, the does-response slope of the second thin-film electrode formed with the palladium conductive layer was found to deviate less than 6%. Finally, when compared to the dose-response slope obtained for the first thin-film electrode formed with the palladium conductive layer, the thin-film electrode formed with the Composition A3 conductive layer deviated less than 8%.

Because the dose-response slopes of the thin-film electrodes formed with the palladium conductive layers and the thin-film electrodes formed with the Composition A3 conductive layers had a maximum observed deviation of less than 8%, it was shown that the electrochemical response (i.e., dose-response) between the two types of thin-film electrodes was substantially similar.

In certain instances, so as to ensure the accuracy of the obtained dose-response slopes, the Type 1 Chronoamperometry Test can be performed for each of the thin-film electrodes under consideration multiple times, and the resulting dose-response slopes for each thin-film electrode can be averaged. In some embodiments, a dose-response slope may be determined for given thin-film electrode at least 5 times, at least 10 times, at least 15 times, at least 20 times, or more, and a final dose-response slope is calculated as the average of such individually-determined dose-response slopes.

Type 1 Linear Sweep Voltammetry Test Description

In addition to the Type 1 Chronoamperometry Test, a Type 1 Linear Sweep Voltammetry Test can be used to test the electrochemical response of the thin-film electrodes. The Type 1 Linear Sweep Voltammetry Test comprises the following steps: 50 mL of 10 mM potassium phosphate buffer containing 145 mM sodium chloride at pH 7.1 was placed into the electrochemical cell and the electrochemical cell was sealed with stoppers. Gas inlet and outlet fittings, which were associated with the gas flow port, allowed inert gas sparging (i.e., de-aerating) of the buffer solution, via a gas flow of nitrogen, using a medium-porous filter stick. The gas flow port additionally allowed the gas flow to be switched from the filter stick to a headspace-blanketing arrangement. The gas outlet was connected to an oil bubbler to prevent back-diffusion of external gas (e.g., air) into the electrochemical cell. The buffer solution was stirred with a magnetic stirbar while simultaneously sparged with nitrogen for at least 10 minutes before switching the gas flow to a blanketing configuration. No agitation of the buffer solution from sparging or otherwise was otherwise present during the electrochemical experiments conducted via the Type 1 Linear Sweep Voltammetry Test (i.e., the solution was quiescent during electrochemical testing).

A linear sweep voltammetry was performed on the thin-film electrode that comprised the working electrode within the electrochemical cell. The initial voltage potential for linear sweep voltammetry was 0 V versus the open circuit potential (also known as the rest potential), as measured between the working electrode and the reference electrode (i.e., the saturated calomel reference electrode), and after a rest period of at least 10 seconds prior to the voltammetric experiment, the voltage potential was swept anodically at 25 mV per second until a current of at least 50 µA was observed.

Application of Type 1 Linear Sweep Voltammetry Test to Thin-Film Electrodes

A plurality of different thin-film electrodes were tested using the Type 1 Linear Sweep Voltammetry Test. In more detail, a thin-film electrode formed with a conductive layer selected from each of the non-noble metal alloys comprising Compositions A1-A6 listed in Table 1 was tested. Specifically, the following thin-film electrodes were tested: a thin-film electrode formed with a conductive layer of Composition A1, a thin-film electrode formed with a conductive layer of Composition A2, a thin-film electrode formed with a conductive layer of Composition A3, a thin-film electrode formed with a conductive layer of Composition A4, a thin-film electrode formed with a conductive layer of Composition A5, and a thin-film electrode formed with a conductive layer of Composition A6. In addition, a thin-film electrode formed with a conductive layer of gold, and a thin-film electrode formed with a conductive layer of palladium were tested.

Figure 10:
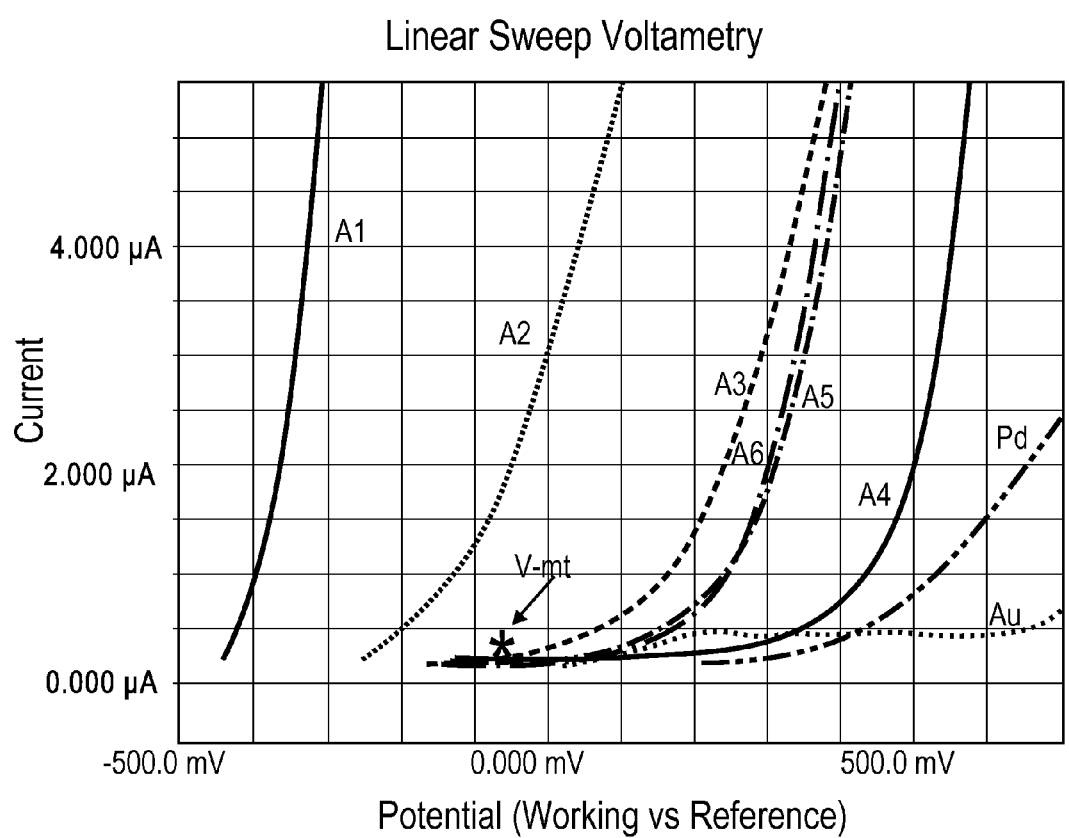
FIG. 10 is a graph depicting linear sweep voltammetry plots of a plurality of thin-film electrodes.

The results of such tests are illustrated graphically in FIG. 10. It may generally be preferable for the thin-film electrodes used in biosensors to exhibit minimized and/or reduced currents under the influence of certain electrode potentials. For instance, it is understood that when the mediator ruthenium (II) hexamine chloride is under the influence of specific electrode potentials within a diffusion controlled current regime, its resulting current is strictly defined by mass transport. It has been determined that such a specific electrode potential for the mediator ruthenium (II) hexamine chloride may be about −60 mV, as measured versus the saturated calomel reference electrode (i.e., V-mt as illustrated on FIG. 10). As such, it is preferable for thin-film electrodes to have negligible background currents when a voltage potential of or about V-mt, as measured versus a saturated calomel reference electrode, is applied to the thin-film electrode. As illustrated in FIG. 10, each of the thin-film electrodes formed from Compositions A3-A6, palladium, and gold have a negligible background current (e.g., less than 0.5 µA) when a voltage potential of less than or equal to V-mt, as measured versus a saturated calomel reference electrode, is applied. In other instances, other mediators may have a diffusion control regime that is associated with other electrode potentials. For instance, such other electrode potentials may be significantly higher than the V-mt illustrated in FIG. 10. As such, it may be preferable for biosensors to use thin-film electrodes that exhibit negligible background currents at electrode potentials significantly higher than V-mt. For instance, the thin-film electrode formed with a Composition A4 conductive layer has a negligible background current (e.g., less than 0.5 µA) when an electrode potential of less than or equal to 300 mV, as measured versus a saturated calomel reference electrode, is applied.

The above detailed description of embodiments of the disclosure is intended to describe various aspects of the invention in sufficient detail to enable those skilled in the art to practice the invention. Other embodiments can be utilized and changes can be made without departing from the scope of the invention. The above detailed description is, therefore, not to be taken in a limiting sense. The scope of the present invention is defined only by claims presented in subsequent regular utility applications, along with the full scope of equivalents to which such claims are entitled.

In this description, references to "one embodiment," "an embodiment," or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, step, etc. described in one embodiment may also be included in other embodiments, but is not necessarily included. Thus, the present technology can include a variety of combinations and/or integrations of the embodiments described herein.

The inventors hereby state their intent to rely on the Doctrine of Equivalents to determine and assess the reasonably fair scope of the present disclosure as it pertains to any apparatus not materially departing from but outside the literal scope of the invention as set forth in the following claims.

DEFINITIONS

It should be understood that the following is not intended to be an exclusive list of defined terms. Other definitions may be provided in the foregoing description, such as, for example, when accompanying the use of a defined term in context.

As used herein, the terms "a," "an," and "the" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," and "have" have the same open-ended meaning as "comprising," "comprises," and "comprise" provided above.

As used herein, the terms "including," "include," and "included" have the same open-ended meaning as "comprising," "comprises," and "comprise" provided above.'

Numerical Ranges

The present description uses numerical ranges to quantify certain parameters relating to the invention. It should be understood that when numerical ranges are provided, such ranges are to be construed as providing literal support for claim limitations that only recite the lower value of the range as well as claim limitations that only recite the upper value of the range. For example, a disclosed numerical range of 10 to 100 provides literal support for a claim reciting "greater than 10" (with no upper bounds) and a claim reciting "less than 100" (with no lower bounds).

What is claimed is:

1. A biosensor component for use in analyzing a biological sample, said biosensor component comprising:
   a substrate;
   a conductive layer coated on said substrate; and
   a biological reactant for electrochemically reacting with said biological sample,
   wherein said conductive layer comprises nickel, chromium, iron, and molybdenum,
   wherein a combined weight percent of the nickel and chromium in the conductive layer is in the range of 50 to 98 weight percent,
   wherein the weight percent of iron in the conductive layer is at least 2 weight percent, and
   wherein the weight percent of molybdenum in the conductive layer is in the range of 2 to 20 weight percent.

2. The biosensor component according to claim 1, wherein said biosensor component comprises an electrode.

3. The biosensor component according to claim 2, wherein said electrode is a working electrode or a reference electrode.

4. The biosensor component according to claim 1, wherein the biosensor is a blood glucose sensor.

5. The biosensor component according to claim 1, wherein said biosensor component comprises a test-strip.

6. The biosensor component according to claim 1, wherein said substrate has a thickness between 25 and 500 µm and said conductive layer has a thickness between 15 and 200 nm.

7. The biosensor component according to claim 1, wherein said conductive layer is physical vapor deposited on said substrate.

8. The biosensor component according to claim 1, wherein said conductive layer meets the compositional criteria of one or more of Compositions A3-A6 set forth in Table 1.

9. The biosensor component according to claim 1, wherein said substrate comprises a flexible, non-conductive film.

10. The biosensor component according to claim 1, wherein said substrate comprise polyethylene terephthalate (PET).

11. The biosensor component according to claim 1, wherein said biosensor component has a visible light transmission of no more than 20%.

12. The biosensor component according to claim 1, wherein said biosensor component has a sheet resistance of no more than 100 ohms per square.

13. The biosensor component according to claim 1, wherein the weight percent of nickel in the conductive layer is at least 50 weight percent, wherein the weight percent of chromium in the conductive layer is at least 15 weight percent, wherein the weight percent of iron in the conductive layer is at least 2 weight percent, and wherein the weight percent of molybdenum is at least 7 weight percent and not more than 17 weight percent.

14. The biosensor component according to claim 1, wherein a combined weight percent of the nickel and chromium in the conductive layer is in the range of 50 to 94 weight percent, wherein the weight percent of nickel in the conductive layer is at least 55 weight percent and not more than 60 weight percent, wherein the weight percent of chromium in the conductive layer is at least 15 weight percent and not more than 34 weight percent, wherein the weight percent of iron in the conductive layer is at least 2 weight percent and not more than 5 weight percent, wherein the weight percent of molybdenum in the conductive layer is at least 7 weight percent and not more than 17 weight percent.

15. The biosensor component of claim 1, wherein the biological reactant is an enzyme, a cofactor, or an enzyme-cofactor complex.

16. The biosensor component of claim 1, wherein the biological reactant comprises an enzyme.

17. The biosensor component of claim 1, wherein the biological sample comprises blood and the biological reactant reacts with glucose in the blood.

18. The biosensor component of claim 1, wherein the conductive layer comprises from 7 up to 17 weight percent molybdenum and up to 0.1 weight percent carbon.

19. The biosensor component of claim 1, wherein the conductive layer is constructed of a single layer of an alloy comprising nickel, chromium, iron, and, optionally, carbon components, wherein the single layer exhibits no distinct boundary between the components of the alloy.

20. A biosensor component for use in analyzing a biological sample, said biosensor component comprising:
   a substrate;
   a conductive layer coated on said substrate; and
   a biological reactant for electrochemically reacting with said biological sample,
   wherein said conductive layer comprises nickel, chromium, iron, and molybdenum,
   wherein the weight percent of nickel in the conductive layer is in the range of 30 to 95 percent,
   wherein the weight percent of chromium in the conductive layer is in the range of 0.5 to 60 weight percent,
   wherein the weight percent of iron in the conductive layer is in the range of 0.25 to 6 weight percent,
   wherein the weight percent of molybdenum in the conductive layer is in the range of 2 to 20 weight percent,
   wherein a combined weight percent of the nickel and chromium in the conductive layer is at least 50 weight percent.

21. The biosensor component according to claim 20, wherein the weight percent of nickel in the conductive layer is at least 50 weight percent, wherein the weight percent of chromium in the conductive layer is at least 15 weight percent, wherein the weight percent of iron in the conductive layer is at least 2 weight percent and not more than 6 weight percent.

22. The biosensor component according to claim 21, wherein the combined weight percent of the nickel and chromium in the conductive layer is at least 73 weight percent.

23. The biosensor component according to claim 20, wherein the weight percent of nickel in the conductive layer is at least 55 weight percent and not more than 60 weight percent.

24. The biosensor component according to claim 20, wherein the weight percent of chromium in the conductive layer is at least 15 weight percent and not more than 35 weight percent.

25. The biosensor component according to claim 20, wherein the weight percent of iron in the conductive layer is at least 0.25 weight percent and not more than 5 weight percent.

26. The biosensor component according to claim 20, wherein the weight percent of nickel in the conductive layer is at least 55 weight percent and not more than 60 weight percent, wherein the weight percent of chromium in the conductive layer is at least 15 weight percent and not more than 35 weight percent, wherein the weight percent of iron in the conductive layer is at least 2 weight percent and not more than 5 weight percent, wherein the weight percent of carbon in the conductive layer is 0-0.1 weight percent.

27. The biosensor component according to claim 26, wherein a combined weight percent of the nickel and chromium in the conductive layer is at least 73 weight percent.

28. The biosensor component according to claim 20, wherein said substrate has a thickness between 25 and 500 μm and said conductive layer has a thickness between 15 and 200 nm, wherein said substrate comprises a flexible, non-conductive film, wherein said biosensor component has a visible light transmission of no more than 20%, wherein said biosensor component has a sheet resistance of no more than 100 ohms per square.

29. The electrode of claim 20, wherein the biological reactant is an enzyme, a cofactor, or an enzyme-cofactor complex.

30. A biosensor component for use in analyzing a biological sample, said biosensor component comprising:
    a substrate;
    a conductive layer coated on said substrate; and
    at least one of i) an enzyme, ii) a cofactor, and iii) an enzyme-cofactor complex,
    wherein said conductive layer comprises nickel, chromium, iron, and molybdenum,
    wherein a combined weight percent of the nickel and chromium in the conductive layer is in the range of 50 to 98 weight percent,
    wherein the weight percent of iron in the conductive layer is at least 2 weight percent, and
    wherein the weight percent of molybdenum in the conductive layer is in the range of 2 to 20 weight percent.

31. The biosensor component of claim 30, wherein the biological sample is blood and the enzyme, cofactor, or enzyme-cofactor complex reacts with glucose in the blood.

* * * * *